US010246743B2

(12) United States Patent
Davis et al.

(10) Patent No.: US 10,246,743 B2
(45) Date of Patent: Apr. 2, 2019

(54) METHODS FOR FORMING LIPID BILAYERS ON BIOCHIPS

(71) Applicant: Genia Technologies, Inc., Santa Clara, CA (US)

(72) Inventors: Randall W. Davis, Pleasanton, CA (US); Edward Shian Liu, Saratoga, CA (US); Eric Takeshi Harada, San Jose, CA (US); Anne Aguirre, San Jose, CA (US); Andrew Trans, Mt. View, CA (US); James Pollard, Mt. View, CA (US); Cynthia Cech, Newcastle, WA (US)

(73) Assignee: GENIA TECHNOLOGIES, INC., Santa Clara, CA (US)

( * ) Notice: Subject to any disclaimer, the term of this patent is extended or adjusted under 35 U.S.C. 154(b) by 84 days.

(21) Appl. No.: 15/385,779

(22) Filed: Dec. 20, 2016

(65) Prior Publication Data
US 2017/0198343 A1 Jul. 13, 2017

Related U.S. Application Data

(63) Continuation of application No. 14/521,425, filed on Oct. 22, 2014, now Pat. No. 9,567,630.
(Continued)

(51) Int. Cl.
*G01N 27/447* (2006.01)
*C12Q 1/6869* (2018.01)
(Continued)

(52) U.S. Cl.
CPC ............ *C12Q 1/6869* (2013.01); *C12M 1/34* (2013.01); *G01N 27/3277* (2013.01);
(Continued)

(58) Field of Classification Search
None
See application file for complete search history.

(56) References Cited

U.S. PATENT DOCUMENTS 7,217,520 B2   5/2007   Tsinberg et al.
7,833,396 B2   11/2010  Fukushima
(Continued)

FOREIGN PATENT DOCUMENTS

JP   2005164388   6/2005
JP   2011160718   8/2011
(Continued)

OTHER PUBLICATIONS

Burns et al., "Self-Assembled DNA Nanopores That Span Lipid Bilayers", Nano Letters, vol. 13, No. 6, Jun. 12, 2013, pp. 2351-2356.
(Continued)

*Primary Examiner* — J. Christopher Ball
(74) *Attorney, Agent, or Firm* — FisherBroyles, LLP; Jason M. Pass; Victoria L. Boyd

(57) ABSTRACT

This disclosure provides a biochip comprising a plurality of wells. The biochip includes a membrane that is disposed in or adjacent to an individual well of the plurality of wells. The membrane comprises a nanopore, and the individual well comprises an electrode that detects a signal upon ionic flow through the pore in response to a species passing through or adjacent to the nanopore. The electrode can be a non-sacrificial electrode. A lipid bilayer can be formed over the plurality of wells using a bubble.

24 Claims, 22 Drawing Sheets

Related U.S. Application Data

(60) Provisional application No. 61/894,661, filed on Oct. 23, 2013.

(51) Int. Cl.
*C12M 1/34* (2006.01)
*G01N 27/327* (2006.01)
*G01N 33/487* (2006.01)

(52) U.S. Cl.
CPC ... *G01N 27/3278* (2013.01); *G01N 27/44791* (2013.01); *G01N 33/48721* (2013.01)

(56) References Cited

U.S. PATENT DOCUMENTS

| | | |
|---|---|---|
| 9,567,630 B2 | 2/2017 | Davis et al. |
| 2005/0079598 A1 | 4/2005 | Davis |
| 2007/0105089 A1 | 5/2007 | Deutsch |
| 2011/0089957 A1 | 4/2011 | Sheppard, Jr. |
| 2012/0052188 A1 * | 3/2012 | Chen ................ B82Y 5/00 427/8 |
| 2013/0087467 A1 | 4/2013 | Yang |
| 2013/0140192 A1 | 6/2013 | Behrends et al. |
| 2013/0260371 A1 | 10/2013 | Holt |

FOREIGN PATENT DOCUMENTS

| | | |
|---|---|---|
| JP | 2013118852 | 6/2013 |
| WO | 2007116978 A1 | 10/2007 |
| WO | 2008/042018 | 4/2008 |
| WO | WO-2013123450 A1 * | 8/2013 ........... C12Q 1/6869 |

OTHER PUBLICATIONS

Gu et al., "Single molecule sensing by nanopores and nanopore devices", The Analyst, vol. 135, No. 3, Jan. 1, 2010, p. 441.

Yang et al., "Advances in nanopore sequencing technology", Journal of Nanoscience and Nanotechnology, American Scientific Publishers, US, vol. 13, No. 7, Jul. 1, 2013, pp. 4521-4538.

* cited by examiner

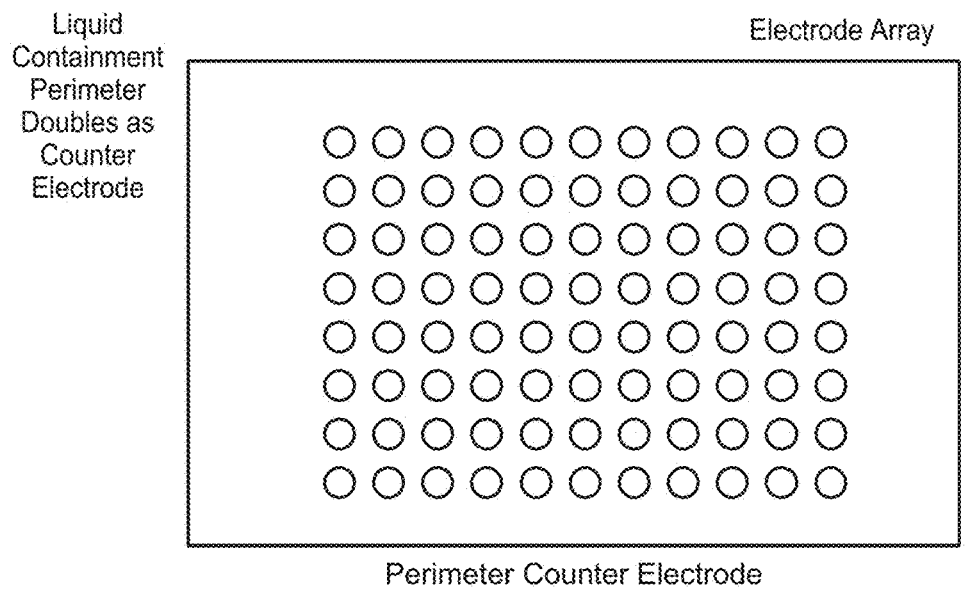
FIG. 3
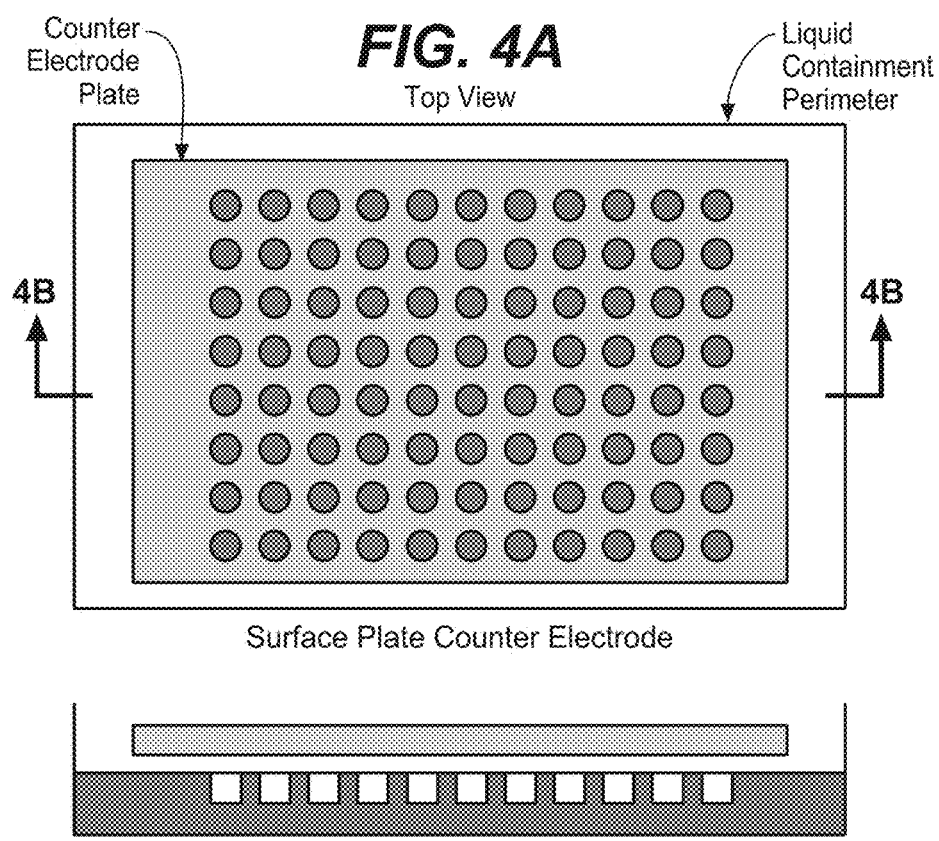
FIG. 4A
FIG. 4B

Independent Counter Electrode Per Channel

Per Cell Counter-Electrode "Moats"

METHODS FOR FORMING LIPID BILAYERS ON BIOCHIPS

CROSS-REFERENCE

This application is a Continuation application that claims the benefit of U.S. patent application Ser. No. 14/521,425, now U.S. Pat. No. 9,567,630, entitled "Methods for Forming Lipid Bilayers on Biochips," filed Oct. 22, 2014, which claims the benefit of U.S. Provisional Application No. 61/894,661, entitled "Methods for Forming Lipid Bilayers on Biochips," filed 23 Oct. 2013, each of which are entirely incorporated herein by reference.

BACKGROUND

Biochips can be used for various kinds of molecular detection and sensing, including the sequencing of nucleic acid molecules. Nucleic acid sequencing is a process that may be used to provide sequence information for a nucleic acid sample. Such sequence information may be helpful in diagnosing and/or treating a subject. For example, the nucleic acid sequence of a subject may be used to identify, diagnose and potentially develop treatments for genetic diseases. As another example, research into pathogens may lead to treatment for contagious diseases.

There are methods available which may be used to sequence a nucleic acid. Such methods, however, are expensive and may not provide sequence information within a time period and at an accuracy that may be necessary to diagnose and/or treat a subject.

SUMMARY

Nanopores can be used to detect various molecules, including but not limited to sequencing polymers such as nucleic acid molecules. Recognized herein is the need for improved biochips and methods for making biochips (e.g., comprising nanopores). In some cases, conventional semiconductor processing techniques are deficient in producing a silicon device for use as a biochip. For instance, methods are provided that can produce a biochip that withstands (e.g., is operable during or after contact with) highly corrosive environments such as aqueous solutions, e.g., comprising ions. In another aspect, the methods described herein create a biochip surface conducive to the formation of organic membranes (e.g., lipid bilayers). In another aspect, the methods provide electrochemical electrodes needed to perform electrical measurements of ionic current flows in the biochip.

Amongst other things, the biochips produced according to the methods described herein can be used for nucleic acid molecule identification and polymer (e.g., nucleic acid) sequencing. In some instances, the polymer is passed through the nanopore and various subunits of the polymer (e.g., adenine (A), cytosine (C), guanine (G), thymine (T) and/or uracil (U) bases of the nucleic acid) affect the current flowing through the nanopore. As described herein, the various subunits can be identified by measuring the current at a plurality of voltages applied across the nanopore and/or membrane. In some cases, the polymerization of tagged nucleotides releases and/or presents tag molecules to the nanopore that can be identified by measuring the current at a plurality of voltages applied across the nanopore and/or membrane.

In an aspect, the disclosure provides a method for forming a lipid bilayer for use in a nanopore sensing device, comprising: (a) providing a chip comprising a fluid flow path in fluid communication with a plurality of sensing electrodes; (b) flowing a lipid solution into the fluid flow path; and (c) flowing at least one bubble onto the fluid flow path, thereby forming a lipid bilayer adjacent to the sensing electrodes, wherein the bubble spans the plurality of sensing electrodes, and wherein the bubble is adjacent to the sensing electrodes for at least about 1 second. In some embodiments, the bubble is adjacent to the sensing electrodes for between about 1 ms to about 5 minutes.

In some embodiments, the bubble is adjacent to the sensing electrodes for at least about 30 seconds. In some embodiments, the bubble is adjacent to the sensing electrodes for at most about 5 minutes. In some embodiments, a lipid bilayer is formed over at least 50% of the sensing electrodes. In some embodiments, a lipid bilayer is formed over at least 70% of the sensing electrodes.

In some embodiments, the method further comprises inserting a nanopore into the lipid bilayers adjacent to each of the sensing electrodes. In some embodiments, the chip comprises wells, and wherein the sensing electrodes are in the wells.

In another aspect, the disclosure provides a method for forming a lipid bilayer for use in a nanopore sensing device, comprising: (a) providing a chip comprising a fluid flow path in fluid communication with a plurality of sensing electrodes; (b) flowing at least one bubble into the fluid flow path and adjacent to said plurality of sensing electrodes such that the bubble spans the plurality of sensing electrodes; and (c) contacting the periphery of the bubble with a lipid, wherein the lipid diffuses under the bubble and onto the fluid flow path, thereby forming a lipid bilayer adjacent to the sensing electrodes.

In some embodiments, the bubble is contacted with the lipid for at least about 30 seconds. In some embodiments, the bubble is contacted with the lipid for between about 5 ms to about 5 minutes. In some embodiments, a lipid bilayer is formed over at least 70% of the sensing electrodes. In some embodiments, the method further comprises inserting a nanopore into the lipid bilayers adjacent to each of the sensing electrodes. In some embodiments, the nanopore is *Mycobacterium smegmatis* porin A (MspA), alpha-hemolysin, any protein having at least 70% homology to at least one of *Mycobacterium smegmatis* porin A (MspA) or alpha-hemolysin, or any combination thereof.

In some embodiments, inserting the nanopore comprises applying an electrical stimulus through said electrode to facilitate the insertion of said nanopore in said lipid bilayer. In some embodiments, said lipid bilayer exhibits a resistance greater than about 1 G$\Omega$.

In some embodiments, said lipid bilayer and said nanopore protein together exhibit a resistance of about 1 G$\Omega$ or less. In some embodiments, said lipid comprises an organic solvent. In some embodiments, said bubble is a vapor bubble. In some embodiments, the chip comprises wells, and wherein the sensing electrodes are in the wells.

In some embodiments, said lipid is selected from the group consisting of diphytanoyl-phosphatidylcholine (DPhPC), 1,2-diphytanoyl-sn-glycero-3phosphocholine, 1,2-Di-O-Phytanyl-sn-Glycero-3-phosphocholine (DoPhPC), palmitoyl-oleoyl-phosphatidyl-choline (POPC), dioleoyl-phosphatidyl-methylester (DOPME), dipalmitoyl-phosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy(polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-1000]; 1,2-dipalmitoyl-sn-glycero-3-phosphoethanolamine-N-[methoxy(polyethylene glycol)-2000]; 1,2-dioleoyl-sn-glycero-3-phosphoethanolamine-N-lactosyl; GM1 Ganglioside, Lysophosphatidylcholine (LPC) or any combination thereof.

In another aspect, the disclosure provides a nanopore sensing system, comprising: (a) a chip comprising a fluid flow path in fluid communication with a plurality of sensing electrodes, wherein each of said sensing electrodes is configured to detect an ionic current upon a nucleic acid incorporation event; and (b) a control system coupled to said chip, said control system programmed to: (i) flow a lipid solution into the fluid flow path; (ii) flow at least one bubble into the fluid flow path and adjacent to the sensing electrodes for a time period of at least about 1 second, wherein the bubble spans the plurality of sensing electrodes, and wherein the flow of the bubble into the fluid flow path forms a lipid bilayer adjacent to the sensing electrodes. In some embodiments, the bubble is adjacent to the sensing electrodes for a time period of between about 5 ms to about 5 minutes.

In some embodiments, the chip comprises wells, and wherein the sensing electrodes are in the wells. In some embodiments, the control system is external to said chip. In some embodiments, the control system comprises a computer processor. In some embodiments, the method further comprises a fluid flow system operably coupled to said control system and said chip, wherein said fluid flow system is configured to direct the flow of said lipid solution and said bubble.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 shows an electrode array where the container doubles as a counter electrode;
FIG. 4A shows a top view of an electrode array with a common counter electrode,
and FIG. 4B shows a cross-section view of the electrode array with a common counter electrode of FIG. 4A.

DETAILED DESCRIPTION

Figure 1:
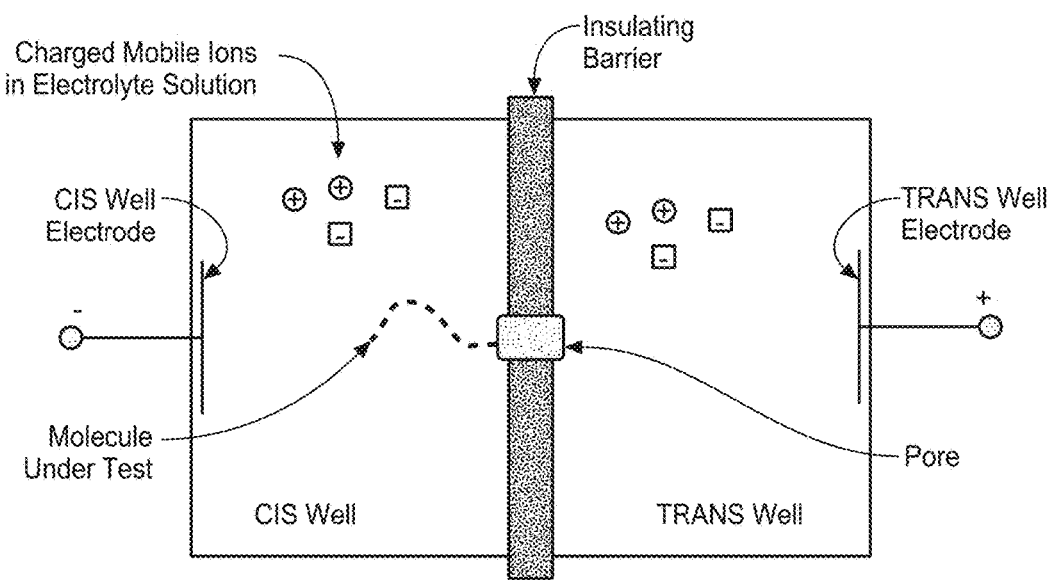
FIG. 1 shows a pore-based electrosensor.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "nanopore," as used herein, generally refers to a pore, channel or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha hemolysin is an example of a protein nanopore.

The term "polymerase," as used herein, generally refers to any enzyme capable of catalyzing a polymerization reaction. Examples of polymerases include, without limitation, a nucleic acid polymerase or a ligase. A polymerase can be a polymerization enzyme.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or derivatives thereof. A nucleic acid may be single-stranded or double stranded.

A "polynucleotide" or "oligonucleotide" is a polymer or oligomer comprising one or more nucleotide as defined herein. A polynucleotide or oligonucleotide may comprise a DNA polynucleotide or oligonucleotide, a RNA polynucleotide or oligonucleotide, or one or more sections of DNA polynucleotide or oligonucleotide and/or RNA polynucleotide or oligonucleotide.

As used herein, a "nucleotide" or "base" can be a primary nucleotide or a nucleotide analog. A primary nucleotide is deoxyadenosine mono-phosphate (dAMP), deoxycytidine mono-phosphate (dCMP), deoxyguanosine mono-phosphate (dGMP), deoxythymidine mono-phosphate (dTMP), adenosine mono-phosphate (AMP), cytidine mono-phosphate (CMP), guanosine mono-phosphate (GMP) or uridine mono-phosphate (UMP). A nucleotide analog is an analog or mimic of a primary nucleotide having modification on the primary nucleobase (A, C, G, T and U), the deoxyribose/ribose structure, the phosphate group of the primary nucleotide, or any combination thereof. For example, a nucleotide analog can have a modified base, either naturally existing or man-made. Examples of modified bases include, without limitation, methylated nucleobases, modified purine bases (e.g., hypoxanthine, xanthine, 7-methylguanine, isodG), modified pyrimidine bases (e.g., 5,6-dihydrouracil and 5-methylcytosine, isodC), universal bases (e.g., 3-nitropyrrole and 5-nitroindole), non-binding base mimics (e.g., 4-methylbezimidazole and 2,4-diflurotoluene or benzene), and no base (abasic nucleotide where the nucleotide analog does not have a base). Examples of nucleotide analogs having modified deoxyribose (e.g., dideoxynucleosides such as dideoxyguanosine, dideoxyadenosine, dideoxythymidine, and dideoxycytidine) and/or phosphate structure (together referred to as the backbone structure) includes, without limitation, glycol nucleotides, morpholinos, and locked nucleotides.

The term "% homology" is used interchangeably herein with the term "% identity" herein and refers to the level of nucleic acid or amino acid sequence identity between the nucleic acid sequence that encodes any one of the inventive polypeptides or the inventive polypeptide's amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for any one of the inventive polypeptides, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, S. F., et al., Nucleic Acids Res. 25:3389-3402, 1997.)

A preferred alignment of selected sequences in order to determine "% identity" between two or more sequences, is performed using for example, the CLUSTAL-W program in MacVector version 13.0.7, operated with default parameters, including an open gap penalty of 10.0, an extended gap penalty of 0.1, and a BLOSUM 30 similarity matrix.

Biochips and Nucleic Acid Sequencing

Pore based sensors (e.g., biochips) can be used for electro-interrogation of single molecules. A pore based sensor of the present disclosure can include a nanopore formed in a membrane that is disposed adjacent or in proximity to a sensing electrode. The sensor can include a counter electrode. The membrane includes a trans side (i.e., side facing the sensing electrode) and a cis side (i.e., side facing the counter electrode).

Reference will now be made to the figures, wherein like numerals refer to like parts throughout. It will be appreciated that the figures and features therein are not necessarily drawn to scale.

With reference to FIG. 1, a typical electrical measurement can operate on a molecule under test that is closely associated with a pore (e.g., binding can be chemical, mechanical, electrical, or electrochemical). The system can apply a stimulus (voltage or current) across the molecule/pore complex and measure the response. In order to isolate the measurement to the pore/molecule complex the two sides of the pore are generally separated by a highly insulating material (e.g., a lipid bilayer).

The volumes enclosed on the opposite sides of the insulating barrier are referred to as the cis well and the trans well with the general definition that the species of interest (e.g., the nucleic acid molecule or tag molecule) moves from cis to trans during detection. The trans well is generally the side of the insulating membrane proximal to and electrically connected to the chip electrodes.

Figure 2:
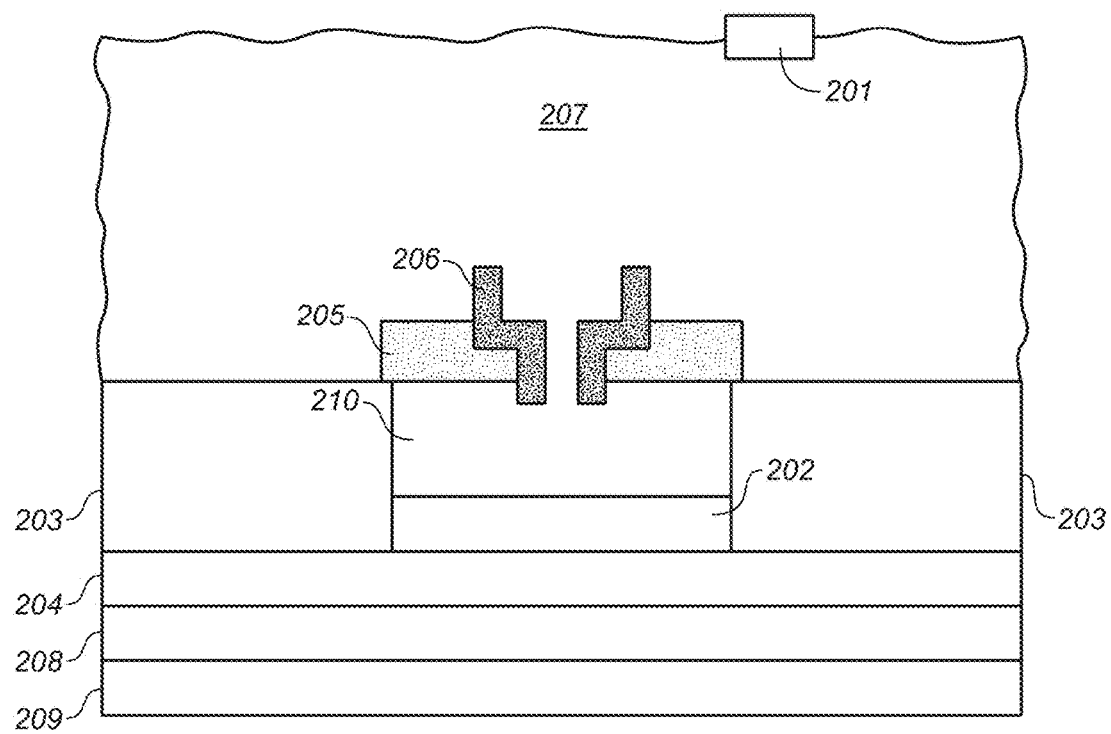
FIG. 2 shows a nanopore biochip.

FIG. 2 shows an example of a nanopore biochip (or sensor) having temperature control, as may be prepared according to methods described in U.S. Patent Application Publication No. 2011/0193570, which is entirely incorporated herein by reference. With reference to FIG. 2, the nanopore detector comprises a top electrode 201 in contact with a conductive solution (e.g., salt solution) 207. A bottom conductive electrode 202 is near, adjacent, or in proximity to a nanopore 206, which is inserted in a membrane 205. The membrane 205 can be disposed over a well 210, or directly over an electrode, where the sensor 202 forms part of the surface of the well. In some instances, the bottom conductive electrode 202 is embedded in a semiconductor 203 in which is embedded electrical circuitry in a semiconductor substrate 204. A surface of the semiconductor 203 may be treated to be hydrophobic. A molecule being detected goes through the pore in the nanopore 206. The semiconductor chip sensor is placed in package 208 and this, in turn, is in the vicinity of a temperature control element 209. The temperature control element 209 may be a thermoelectric heating and/or cooling device (e.g., Peltier device). Multiple nanopore detectors may form a nanopore array.

Figure 5:
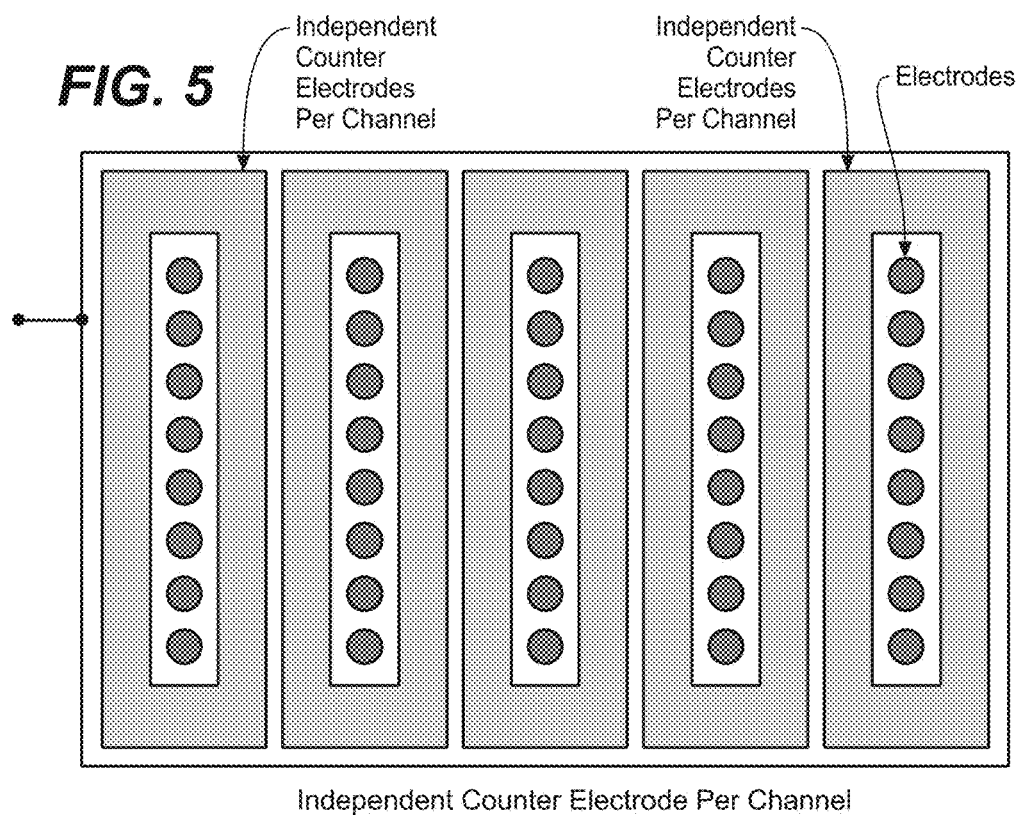
FIG. 5 shows an electrode array where strips of sensors share a common counter electrode.
Figure 6:
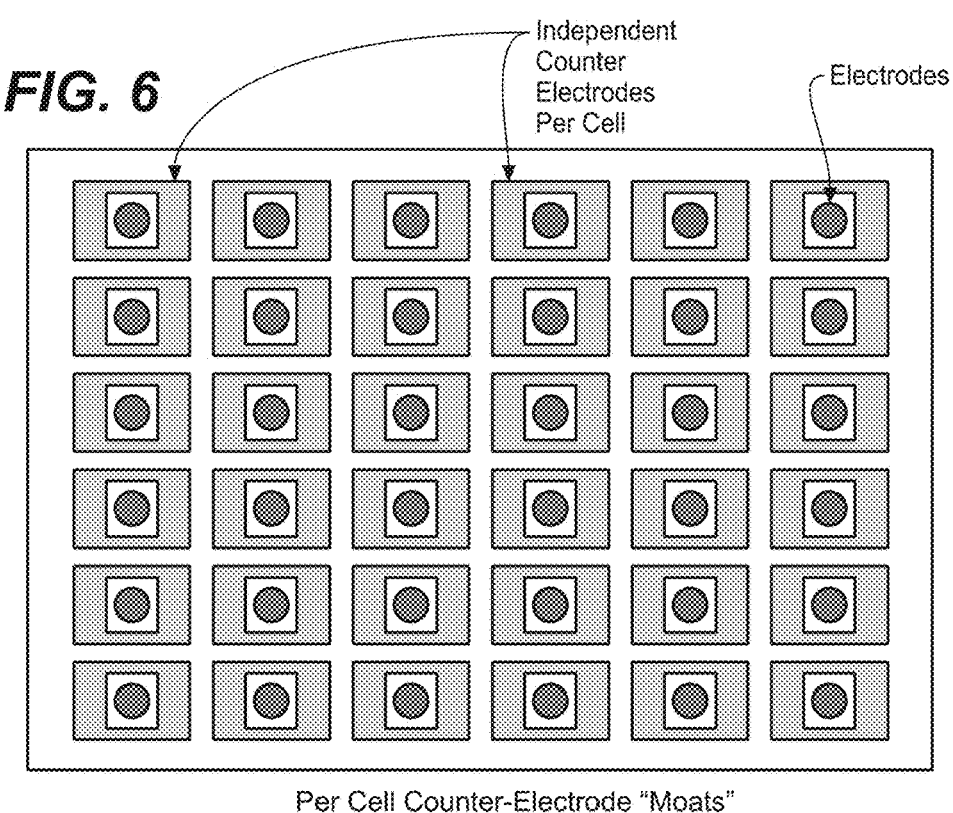
FIG. 6 shows and electrode array where each electrode has an independent counter electrode.

In some embodiments, the biochip comprises a counter electrode capable of forming an electrical circuit with the electrode in the well. In some cases, the plurality of electrodes in the plurality of wells share a common counter electrode. FIG. 3 shows an electrode array having a common counter electrode where the liquid containment perimeter (e.g., container) acts as a counter electrode (e.g., is conductive and forms a circuit). Another embodiment of a counter electrode is shown in FIG. 4A (top view) and FIG. 4B (cross-section view), where the counter electrode is a plate (e.g., made of a conducting metal) over top of the nanopores. As shown in FIG. 5 and FIG. 6, the plurality of electrodes in the plurality of wells can be organized into groups that share a common counter electrode. In some cases, (e.g., FIG. 6), the plurality of electrodes in the plurality of wells each have a dedicated counter electrode. In some cases, having a plurality of counter electrodes can allow an individual sensing electrode, or only a few sensing electrodes, to be paired with a single counter electrode and thus potentially improve the electrical response and performance of the sense-counter electrode pairs.

Figure 7:
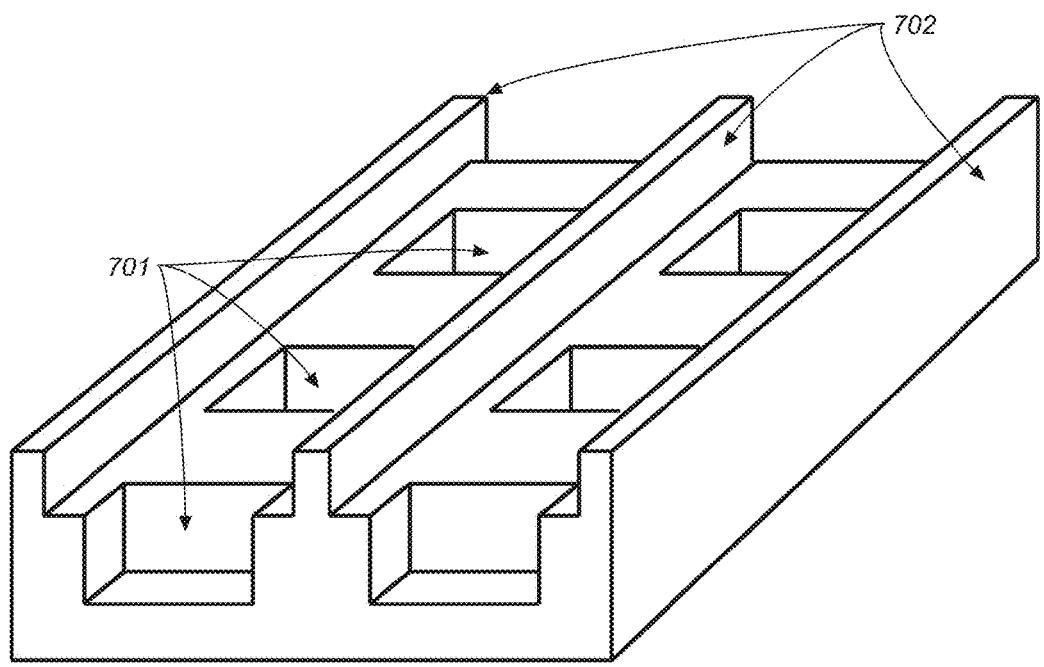
FIG. 7 shows an example of rows of sensor wells sharing a common electrolyte pool.

In some cases, a plurality of wells (including any subset of the total number of wells) comprise a common electrolyte pool. As shown in FIG. 7, the wells 701 may be separated into rows by walls 702 such that the row of wells share a common electrolyte pool above the wells. Separating the biochip into sections as described here can allow multiple samples to be analyzed on a single biochip (e.g., by putting different samples in different sections of the chip).

A nanopore sensor can include at least 1, 2, 3, 4, 5, 6, 7, 8, 9, 10, 20, 30, 40, 50, 100, or 1000 nanopores (e.g., hemolysin or aquaporin, etc. or combinations thereof) adjacent to a electrode (e.g., the bottom conductive electrode 202). A nanopore sensor can include a top electrode (e.g., the top electrode 201) that is for sole use by the nanopore sensor (and not other sensors), or as an alternative, a top electrode can be provided for use by multiple nanopore sensors.

Biochip Processing

Controlling surface characteristics, well cavity volume, and electrode composition and volume can be major challenges of developing a scalable semiconductor based planar array of microwells for the purpose of nanopore sensing. In some instances, the ideal nanopore based semiconductor array sensing platform would achieve the following goals: (1) chip surface characteristics that support a planar insulating membrane, (2) differentiated surface characteristics that result in a well-defined and well controlled planar membrane surface, (3) large trans-well electrolyte volume, (4) large electrode volume, (5) low electrical cross-talk between adjacent sensor electrodes on the array, (6) high cell density in order to achieve very large array sizes, and (7) stable measurements of very long duration during which the key parameters (voltage, resistance, etc.) remain nearly constant.

For example meeting goals (1) & (2) can be difficult as in particular it can be necessary to ensure that a highly insulating (resistive) barrier is formed with well controlled membrane areas and trans-well volumes.

In the case of forming a lipid bilayer membrane, the design and processing of the chip can be tailored to create hydrophobic (or lipophilic) surfaces and hydrophilic (or lipophobic) surfaces. Careful control of the chip surface allows well defined hydrophilic and hydrophobic areas to be defined. In turn this can control the structure and characteristics of the lipid bilayer membranes formed.

Goal (3) can be important in order to ensure that trans-well electrolytic ions are sufficiently abundant so as not to affect the results during the duration of a typical measurement. This could occur either by depleting one or the other of the ions entirely or shifting the relative concentration of the various ions to such a degree that they change the measurement results substantially (i.e., through shifts in concentration gradient and resulting Nernst potential).

Goal (4) can be important in the case of a sacrificial electrode that is consumed or converted as part of the electro-chemical reaction that supports the measurement (e.g. silver being converted to silver-chloride oxidation reaction). Having a high electrode volume can be important both to: (i) increase the time that a measurement can be continuously performed without intervening "recharging" measurements which may disrupt the experiment completely or result in gaps in the measured data and (ii) reduce electrochemical potential shifts caused by the change in relative concentrations of the oxidized and reduced electrode components. In some cases, complete depletion of the electrode material (silver) sets a theoretical upper boundary on practical continuous measurement duration.

Unfortunately several of these goals can result in conflicts where meeting one goal comes at the expense of another. For example, etching a deep cavity in the silicon surface and filling completely with silver can achieve a planar membrane at the metal/silicon surface, thereby achieving goals (1), (2), and (4) however leaves no remaining volume available for trans-well electrolyte. Similarly, minimizing electrical cross-talk (goal 5) can be achieved by spacing adjacent cells far apart; however this comes at the expense of achieving goal (6).

In various aspects, the biochips and methods for making biochips described herein can achieve goals (1) to (6) in a way that is capable of sequencing nucleic acid molecules. For example, development of a deep well vertical cavity structure to support both electrolyte and electrode material can meet goals (3) and (4); a hybrid wet/dry etch can increase the lateral dimensions and thus trans well volume in can meet goals (1), (2), (3), and (4); selective silanization of oxide surfaces can achieve goals (1) and (2); utilization of a gel can be used to balance goals (3) and (4) while simultaneously achieving goals (1) and (2); implementation of distributed counter electrode can simultaneously achieve goals (5) and (6); use of electrode replenishment (recharging) can achieve goal (7); use of non-sacrificial electrodes (when feasible) can achieve goal (7); electro-plating can increase electrode material to meet goal (4); or any combination thereof.

Biochip Characteristics

In an aspect, a biochip comprises (a) a semiconductor substrate; (b) a layer of silicon dioxide disposed on the substrate, wherein a well is formed into the silicon dioxide; (c) a corrosion resistant material coating the inside of the well; (d) an electrode material in the well filling some fraction of that well including completely filling the oxide well to be coplanar with the surface of the oxide; and (e) an organofunctional alkoxysilane layer coating the silicon dioxide. In some embodiments, the biochip further comprises a membrane isolating a first fluid in the well from a second fluid outside the well. Also encompassed within the present invention are the biochips made by any of the methods described herein and the use of any of the biochips described herein or biochips produced by the methods described herein to sequence polymers, including but not limited to nucleic acid molecules.

In some cases, electrode material is not depleted during operation of the biochip. In an aspect, a biochip comprises a plurality of wells having a membrane disposed over the well and an electrode in the well that is capable of detecting changes in the flow of ions through a pore in the membrane in response to entities passing through the pore, wherein the electrode is not depleted during detection. In some embodiments, the electrode is substantially planar with the surface of the biochip, i.e., metal fills the entire well.

The electrode (e.g., silver or platinum material) can have any suitable mass or volume. In some cases, the volume of the electrode is about 0.1 femto-liter (fL), about 0.5 fL, about 1 fL, about 5 fL, or about 10 fL. In some instances, the volume of the electrode is at least about 0.1 femto-liter (fL), at least about 0.5 fL, at least about 1 fL, at least about 5 fL, or at least about 10 fL. In some embodiments, the volume of the electrode is at most about 0.1 femto-liter (fL), at most about 0.5 fL, at most about 1 fL, at most about 5 fL, or at most about 10 fL.

The electrode can be made of any suitable material, including mixtures and alloys of materials. Some examples include platinum, silver, or any combination thereof. In some cases, the electrode material is not consumed during operation of the electrode. The electrode can comprise a material that has at least two oxidation states and/or a material that is capable of both accepting and donating electrons.

Chip with Deep, Closely Packed Wells

Having a high density of nanopore sensors on the biochip may be desirable for having a small device and/or sensing or sequencing a large number of molecules with a small biochip device. The surface comprises any suitable density of discrete sites (e.g., a density suitable for sequencing a nucleic acid sample in a given amount of time or for a given cost). In an embodiment, the surface has a density of discrete sites greater than or equal to about 500 sites per 1 $mm^2$. In some embodiments, the surface has a density of discrete sites of about 100, about 200, about 300, about 400, about 500, about 600, about 700, about 800, about 900, about 1000, about 2000, about 3000, about 4000, about 5000, about 6000, about 7000, about 8000, about 9000, about 10000, about 20000, about 40000, about 60000, about 80000, about 100000, or about 500000 sites per 1 $mm^2$. In some embodiments, the surface has a density of discrete sites of at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 20000, at least about 40000, at least about 60000, at least about 80000, at least about 100000, or at least about 500000 sites per 1 $mm^2$.

A biochip with a high density of discrete sites generally results in a well with a small area. In some instances, the well is suitably deep (e.g., such that the well has a suitably large volume). In some instances, the well is substantially co-planar with the chip surface (i.e., metal fills the entire well). In an aspect, the volume of the well is suitably large such that ion concentration is not fully depleted in the well before recharging the electrode. In an aspect, the electrode can be a sacrificial electrode (e.g., an electrode that decreases and/or increases in volume during detection, such as silver) and the volume of the well is suitably large such that the electrode is not fully depleted before recharging the electrode. In some embodiments, the well contains a sufficiently large volume of electrode material such as silver. In these aspects, amongst others, the volume of the well can limit the time for which the electrode is capable of detecting a current (i.e., before an ion is depleted and/or the electrode material is depleted).

In some embodiments, the wells have a suitably large volume such that the electrode can detect ion flow (e.g., current) for about 50 μs, about 100 μs, about 150 μs, about 200 μs, about 250 μs, about 300 μs, about 350 μs, about 400 μs, about 450 μs, about 500 μs, about 550 μs, about 600 μs, about 650 μs, about 700 μs, about 750 μs, about 800 μs, about 850 μs, about 900 μs, about 950 μs, about 1 ms, about 5 ms, about 10 ms, about 50 ms, about 100 ms, about 500 ms, about 1 s, about 5 s, about 10 s, about 50 s, about 100 s, about 500 s, about 1000 s, or about 5000 s. In some embodiments, the wells have a suitably large volume such that the electrode can detect ion flow (e.g., current) for at least about 50 μs, at least about 100 μs, at least about 150 μs, at least about 200 μs, at least about 250 μs, at least about 300 μs, at least about 350 μs, at least about 400 μs, at least about 450 μs, at least about 500 μs, at least about 550 μs, at least about 600 μs, at least about 650 μs, at least about 700 μs, at least about 750 µs, at least about 800 µs, at least about 850 µs, at least about 900 µs, at least about 950 µs, at least about 1 ms, at least about 5 ms, at least about 10 ms, at least about 50 ms, at least about 100 ms, at least about 500 ms, at least about 1 s, at least about 5 s, at least about 10 s, at least about 50 s, at least about 100 s, at least about 500 s, at least about 1000 s, or at least about 5000 s.

By balancing the potential voltage applied across the electrode and thereby recharging or redistributing the ions on either side of the bilayer pore, the data gathering lifetime of the pore may be significantly extended to 10, 20, or 48 hours or longer. An example would be in nanopore system with 300 mM KCl ionic solution at pH7.5, to apply +120 mV across a bilayer pore for 30 seconds and then drop the voltage to −120 mV for 40 seconds. The cycle is repeated in this slow switching DC manner and the ionic charge distribution of the CIS and TRANS side of the bilayer pore remains balanced, as well as the the composition of Ag and AgCl present at one or more silver electrodes also maintains a balance. The result is a long life, data gathering pore detector. The level or magnitude of the positive and negatives voltages and the time spent in + or − polarity can be varied to suit the salt or ionic solution concentrations and the type of pore that is being used.

The time of detection can depend at least in part on the magnitude of the voltage applied across the nanopore and/or membrane (e.g., with higher voltage magnitudes resulting in higher ion current, faster depletion of electrodes and therefore relatively shorter detection periods). In some embodiments, the voltage difference across the membrane is from about 0 mV to about 1V, positive or negative, e.g., about 40 mV, about 60 mV, about 80 mV, about 100 mV, about 120 mV, about 140 mV, about 160 mV, about 180 mV, about 200 mV, about 300 mV, about 400 mV, or about 500 mV. In some embodiments, the voltage difference across the membrane is at most about 40 mV, at most about 60 mV, at most about 80 mV, at most about 100 mV, at most about 120 mV, at most about 140 mV, at most about 160 mV, at most about 180 mV, at most about 200 mV, at most about 300 mV, at most about 400 mV, or at most about 500 mV. In some embodiments, the voltage difference across the membrane is at least about 0 mV to about 1V, positive or negative, e.g., at least about 40 mV, at least about 60 mV, at least about 80 mV, at least about 100 mV, at least about 120 mV, at least about 140 mV, at least about 160 mV, at least about 180 mV, at least about 200 mV, at least about 300 mV, at least about 400 mV, or at least about 500 mV. The voltage can be constant or variable (e.g., varying over any periodic waveform).

In some situations, the electrode has an operating life of at least about 1 minute ("min"), 2 min, 3 min, 4 min, 5 min, 6 min, 7 min, 8 min, 9 min, 10 min, 15 min, 20 min, 30 min, 40 min, 50 min, 1 hour, 2 hours, 3 hours, 4 hours, 5 hours, 6 hours, or 12 hours under an applied potential of at least about 0 mV to about 1V, positive or negative, e.g., about 40 mV, about 60 mV, about 80 mV, about 100 mV, about 120 mV, about 140 mV, about 160 mV, about 180 mV, about 200 mV, about 300 mV, about 400 mV, or about 500 mV. In some examples, the electrode has an operating life of at least about 15 min under an applied potential of about 80 mV.

The operating life of the electrode may be assessed based upon the depletion (e.g., rate of depletion) of the electrode during use. In some cases, the electrode material is depleted by at most about 50%, 40%, 30%, 20%, 10%, 9%, 8%, 7%, 6%, 5%, 4%, 3%, 2%, 1%, 0.1%, or 0.01% within a time period that is less than or equal to about 60 minutes, 30 minutes, 20 minutes, 15 minutes, 10 minutes, 5 minutes, 4 minutes, 3 minutes, 2 minutes, or 1 minute during use of the electrode. In some embodiments, the electrode material is not depleted within a time period that is less than or equal to about 60 minutes, 30 minutes, 20 minutes, 15 minutes, 10 minutes, 5 minutes, 4 minutes, 3 minutes, 2 minutes, or 1 minute during use of the electrode.

The wells can have any suitable depth. In some cases, the depth of the well is measured from the surface of the biochip and/or bottom of the membrane to the top of the electrode and/or bottom of the electrode. In some cases, the depth of the well is approximately equal to the thickness of an oxide layer (e.g., 203 in FIG. 2). In some embodiments, the wells are about 0.5 micrometers (µm), about 1 µm, about 1.5 µm, about 2 µm, about 2.5 µm, about 3 µm, about 3.5 µm, about 4 µm, about 4.5 µm, about 5 µm, about 6 µm, about 7 µm, about 8 µm, about 9 µm, about 10 µm, or about 20 µm deep. In some embodiments, the wells are at least about 0.5 micrometers (µm), at least about 1 µm, at least about 1.5 µm, at least about 2 µm, at least about 2.5 µm, at least about 3 µm, at least about 3.5 µm, at least about 4 µm, at least about 4.5 µm, at least about 5 µm, at least about 6 µm, at least about 7 µm, at least about 8 µm, at least about 9 µm, at least about 10 µm, or at least about 20 µm deep.

In an aspect, a biochip comprises a plurality of wells having a membrane disposed over the well and an electrode in the well that is capable of detecting changes in the flow of ions through a pore in the membrane in response to entities passing through the pore. The biochip can comprise at least 500 wells per square millimeter and the wells can have a suitably large volume such that the electrode can detect at least 100 entities without recharging the electrode.

In some embodiments, the entities are tag molecules detected during nucleotide incorporation events. In some instances, a polymer passes through the pore and the entities are subunits of the polymer. In some cases, the polymer is a nucleic acid and the subunits of the polymer are nucleobases.

The biochip can detect any suitable number of entities without recharging the electrode. In some cases, about 10, about 50, about 100, about 500, about 1000, about 5000, about 10000, about 50000, about 100000, about 500000, about 1000000, about 5000000, or about 10000000 entities are detected. In some cases, at least about 10, at least about 50, at least about 100, at least about 500, at least about 1000, at least about 5000, at least about 10000, at least about 50000, at least about 100000, at least about 500000, at least about 1000000, at least about 5000000, or at least about 10000000 entities are detected.

Chip with Closely Packed Wells and Minimum Cross-Talk

In an aspect, the wells are closely packed and have a low amount of cross-talk (e.g., the electrodes derive all or most of their signal from the nanopore and/or membrane nearest to the electrode). In an aspect, a biochip comprises a plurality of wells having a membrane disposed over the well and an electrode in the well that detects a signal in response to the flow of ions, wherein the biochip comprises at least 500 wells per square millimeter and the electrodes are electrically isolated from each other. The biochip can comprise any suitable number of wells per area as described herein.

In some embodiments, an electrode detects about 80%, about 90%, about 95%, about 99%, about 99.5%, or about 99.9% of its signal from the flow of ions through a nanopore in the membrane. In some instances, the electrode detects at least about 80%, at least about 90%, at least about 95%, at least about 99%, at least about 99.5%, or at least about 99.9% of its signal from the flow of ions through a nanopore in the membrane. In some cases, an electrode detects no more than 20%, no more than 10%, no more than 5%, no more than 1%, no more than 0.5%, or no more than 0.1%, of its signal from the flow of ions through nanopores in adjacent wells.

Methods for Making Biochips

Certain methods can be used to make high quality biochips that are among other things, capable of withstanding corrosive solutions and forming a membrane on the biochip that has a high resistivity. In an aspect, a method for preparing a biochip comprises providing a semiconductor substrate and forming a plurality of wells containing electrodes capable of performing electrical measurements on or adjacent to the substrate where the method further comprises (a) treating the substrate to withstand corrosive solutions; and (b) preparing the substrate for the formation of a membrane that seals the well with a high resistivity.

The membrane can have any suitably high resistivity. In some cases, the resistivity is about 10 mega-ohms (MΩ), about 50 MΩ, about 100 MΩ, about 500 MΩ, about 1 giga-ohm (GΩ), about 5 GΩ, or about 10 GΩ. In some cases, the resistivity is at least about 10 mega-ohms (MΩ), at least about 50 MΩ, at least about 100 MΩ, at least about 500 MΩ, at least about 1 giga-ohm (GΩ), at least about 5 GΩ, or at least about 10 GΩ.

In some embodiments, the semiconductor substrate comprises silicon. In some instances, the membrane is a lipid bilayer. The electrodes can be capable of measuring ionic current flows through a nanopore embedded in the membrane.

The device can withstand any suitable corrosive solution. In some cases, the corrosive solutions are aqueous (include water) and comprise ions (e.g., Na+, Cl−). In some cases, the biochip is operable after contacting for many weeks with 1 M NaCl.

In an aspect, a method for preparing a biochip comprises: (a) depositing a material having reactive oxide groups on a semiconductor substrate; (b) etching wells into the silicon dioxide; (c) forming metal electrodes in the wells; (d) removing metal from all areas of the substrate except for the wells; and (e) coating the substrate with a layer suitable for adhesion of a membrane. In some cases, the semiconductor substrate comprises silicon. The method can prepare the biochip for use in nucleic acid sequencing using a nanopore.

In some embodiments, the material in (a) is silicon dioxide. The material can present a hard, planar surface that exhibits a uniform covering of reactive oxide (—OH) groups to a solution in contact with its surface. These oxide groups can be the attachment points for the subsequent silanization process (e). Alternatively, a lipophillic and hydrophobic surface material can be deposited that mimics the etching characteristics of silicon oxide.

In some embodiments, a passivation layer is deposited on the semiconductor substrate in (a), which may or may not have reactive oxide groups. The passivation layer can comprise silicon nitride (Si3N4) or polymide. In some instances, a photolithographic operation is used to define regions where membranes form on the passivation layer.

FIG. 8 to FIG. 20 show an example of operations that can result in biochips. All figures are not necessarily drawn to scale.

Figure 8:
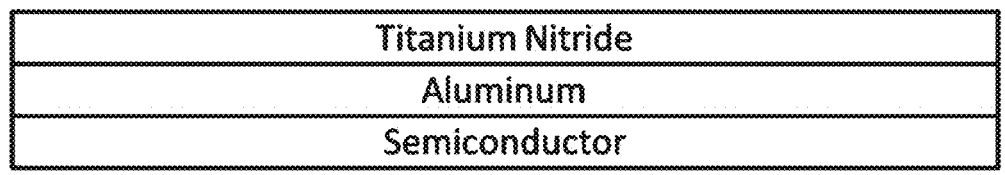
FIG. 8 shows an example of a semiconductor substrate.

With reference to FIG. 8, the method for producing a biochip can start with a semiconductor substrate. The semiconductor (e.g., silicon) can have any number of layers disposed upon it, including but not limited to a metal. The conducting layer is aluminum in some instances. In some cases, the substrate has a protective layer (e.g., titanium nitride). The layers can be deposited with the aid of various deposition techniques, such as, for example, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD) and physical vapor deposition (e.g., sputter deposition, evaporative deposition).

Figure 9:
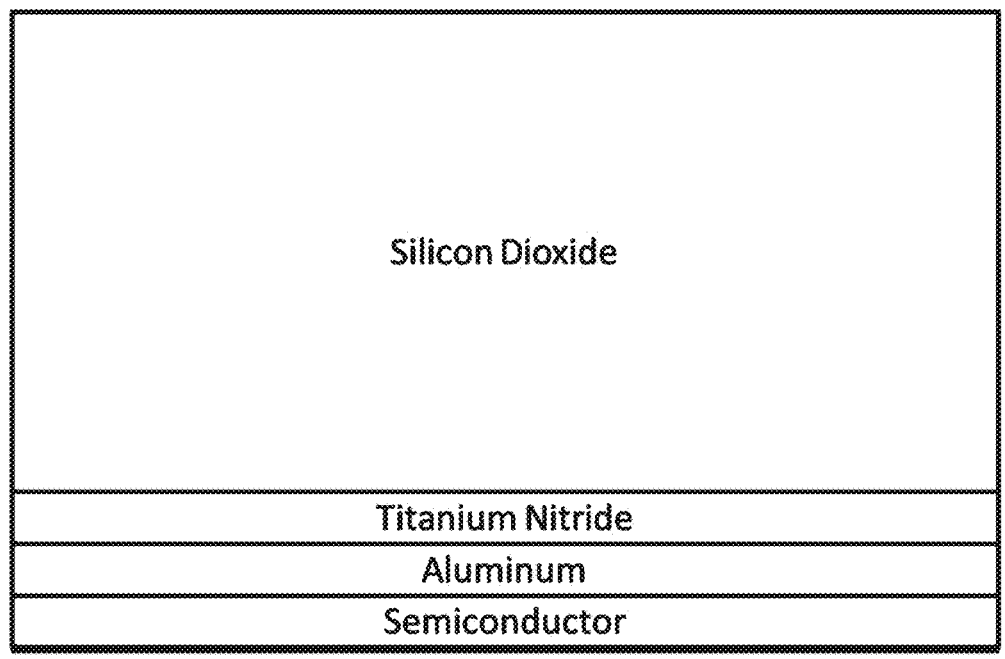
FIG. 9 shows a layer of silicon dioxide deposited on a semiconductor substrate.

In some cases, an oxide layer is deposited on the semiconductor substrate as shown in FIG. 9. In some instances, the oxide layer comprises silicon dioxide. The silicon dioxide can be deposited using tetraethyl orthosilicate (TEOS), high density plasma (HDP), or any combination thereof.

In some instances, the silicon dioxide is deposited using a low temperature technique. In some cases, the process is low-temperature chemical vapor deposition of silicon oxide. The temperature is generally sufficiently low such that pre-exisiting metal on the chip is not damaged. The deposition temperature can be about 50° C., about 100° C., about 150° C., about 200° C., about 250° C., about 300° C., about 350° C., and the like. In some embodiments, the deposition temperature is below about 50° C., below about 100° C., below about 150° C., below about 200° C., below about 250° C., below about 300° C., below about 350° C., and the like. The deposition can be performed at any suitable pressure. In some instances, the deposition process uses RF plasma energy.

In some cases, the oxide is not deposited by a thermally grown oxide procedure (e.g., which can use temperatures near or exceeding 1,000° C.).

The silicon dioxide can be deposited to a thickness suitable for the formation of wells comprising electrodes and a volume of electrolyte capable of sequencing at least 100, at least 1000, at least 10000, at least 100000, or at least 1000000 nucleobases of a nucleic acid molecule without recharging the electrodes.

The silicon dioxide can be deposited to any suitable thickness. In some embodiments, the silicon dioxide is about 0.5 micrometers (μm), about 1 μm, about 1.5 μm, about 2 μm, about 2.5 μm, about 3 μm, about 3.5 μm, about 4 μm, about 4.5 μm, about 5 μm, about 6 μm, about 7 μm, about 8 μm, about 9 μm, about 10 μm, or about 20 μm thick. In some embodiments, the silicon dioxide is at least about 0.5 micrometers (μm), at least about 1 μm, at least about 1.5 μm, at least about 2 μm, at least about 2.5 μm, at least about 3 μm, at least about 3.5 μm, at least about 4 μm, at least about 4.5 μm, at least about 5 μm, at least about 6 μm, at least about 7 μm, at least about 8 μm, at least about 9 μm, at least about 10 μm, or at least about 20 μm thick.

Well Etching

Figure 10:
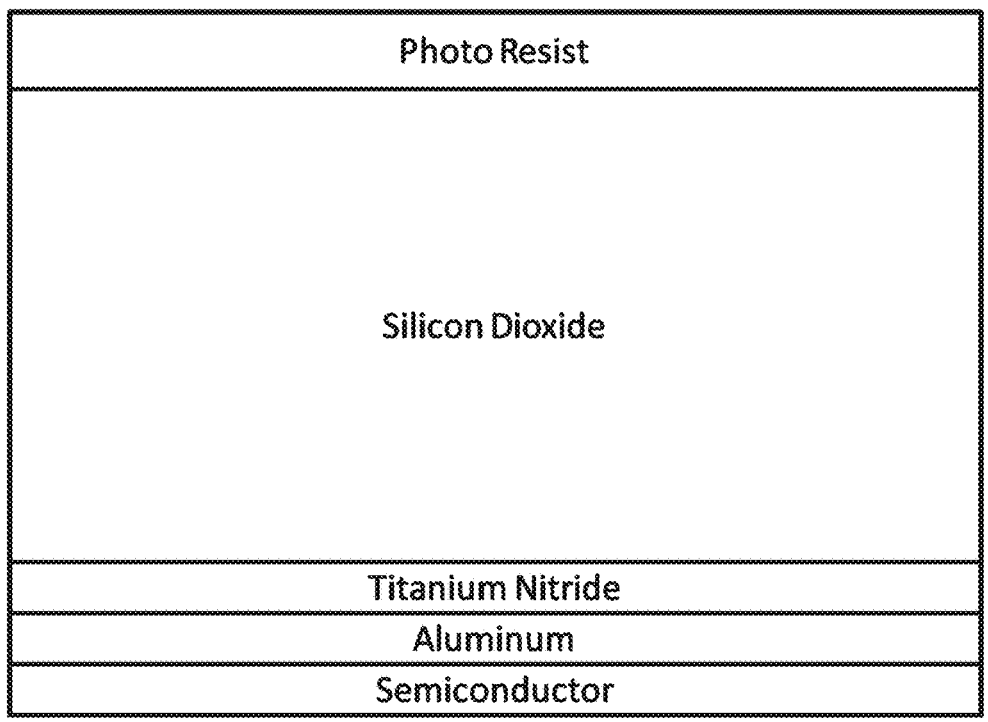
FIG. 10 shows a photo-resist deposited on a silicon dioxide layer.
Figure 11:
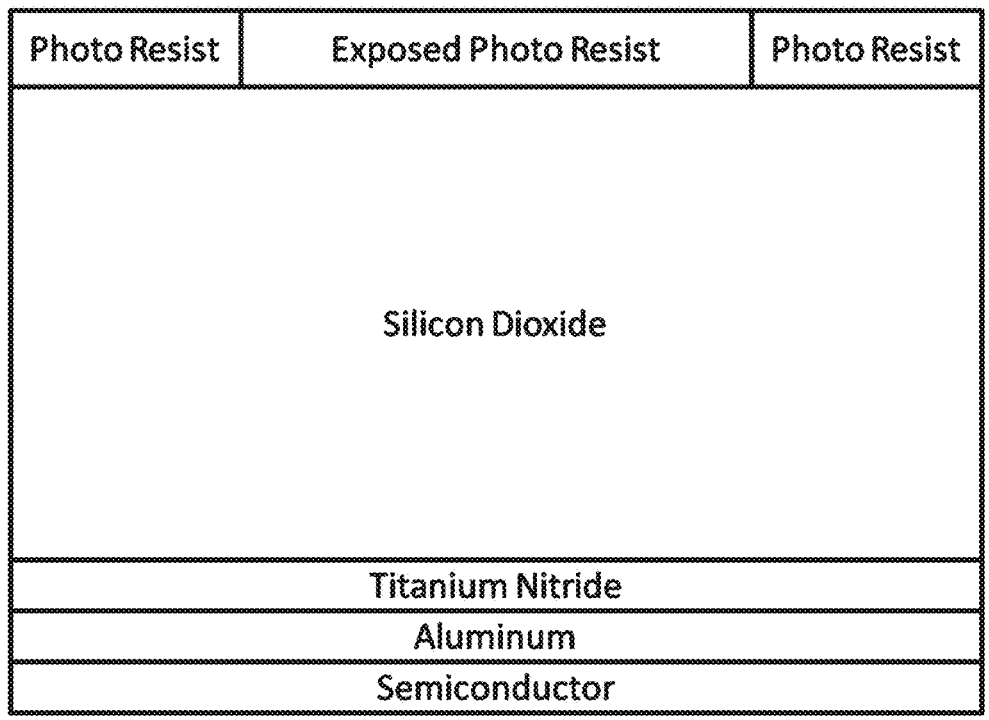
FIG. 11 shows an area of the photo-resist being exposed to radiation to define the area of a well.

Wells can be created in a silicon dioxide substrate using various manufacturing techniques. Such techniques may include semiconductor fabrication techniques. In some cases, the wells are created using photolithographic techniques such as those used in the semiconductor industry. For example, a photo-resist (e.g., a material that changes properties when exposed to electromagnetic radiation) can be coated onto the silicon dioxide (e.g., by spin coating of a wafer) to any suitable thickness as shown in FIG. 10. The substrate including the photo-resist is then exposed to an electromagnetic radiation source. A mask can be used to shield radiation from portions of the photo-resist in order to define the area of the wells. The photo-resist can be a negative resist or a positive resist (e.g., the area of the well can be exposed to electromagnetic radiation or the areas other than the well can be exposed to electromagnetic radiation as defined by the mask). In FIG. 11, the area overlying the location in which the wells are to be created is exposed to electromagnetic radiation to define a pattern that corresponds to the location and distribution of the wells in the silicon dioxide layer. The photoresist can be exposed to electromagnetic radiation through a mask defining a pattern that corresponds to the wells. Next, the exposed portion of the photoresist is removed, such as, e.g., with the aid of a washing operation (e.g., 2% soln of TMAH (tetra methyl ammonium hydroxide) or other solution known to those of skill in the art). The removed portion of the mask can then be exposed to a chemical etchant to etch the substrate and transfer the pattern of wells into the silicon dioxide layer. The etchant can include an acid, such as, for example, sulfuric acid ($H_2SO_4$). The silicon dioxide layer can be etched in an anisotropic fashion, though in some cases etching may be isotropic. For instance, with reference to FIG. 13, an area not corresponding exactly to the area of a final well can be etched (e.g., the well can be etched under the photo-resist).

Figure 12:
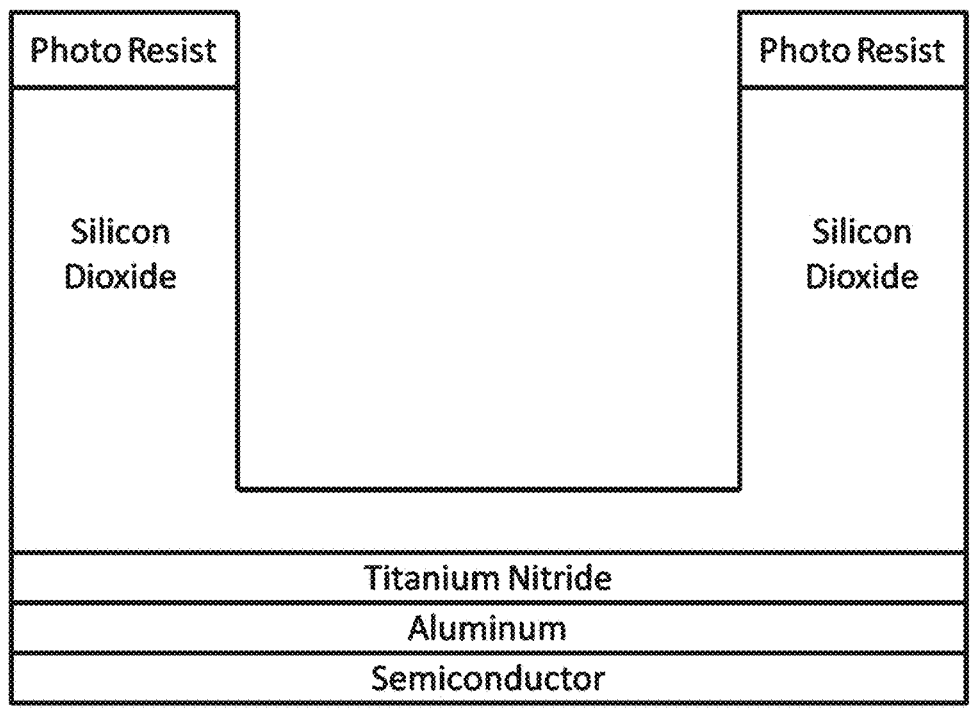
FIG. 12 shows a portion of the silicon dioxide being removed by a dry etch procedure.
Figure 13:
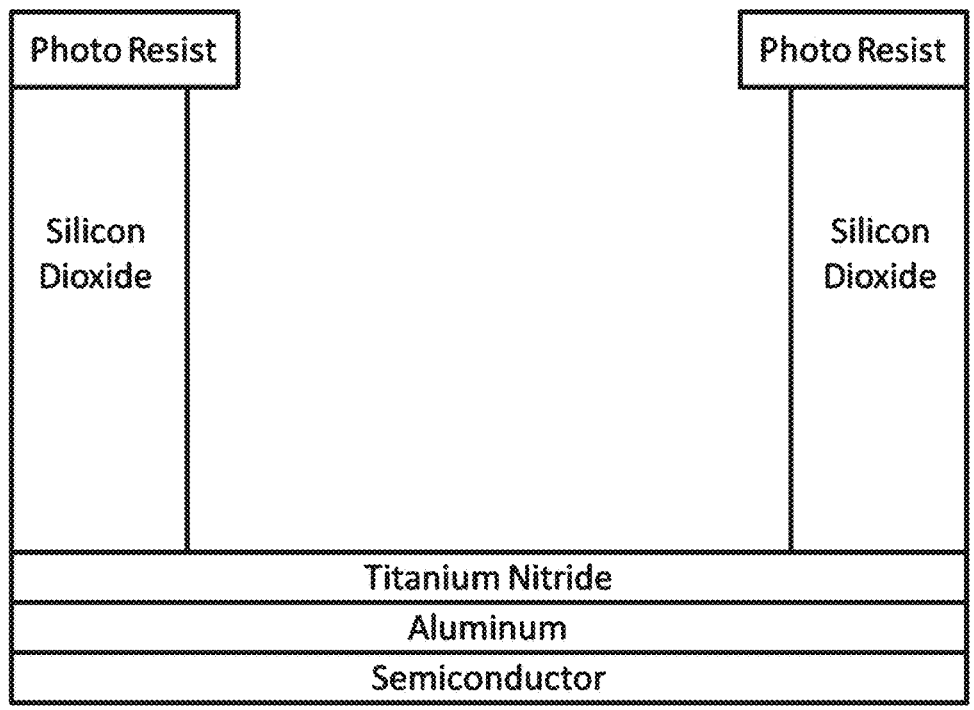
FIG. 13 shows additional silicon dioxide being removed by a wet etch procedure to create a well.

Various etching procedures can be used to etch the silicon dioxide in the area where the well is to be formed. As shown in FIG. 12 and FIG. 13, the etch can be an isotropic etch (i.e., the etch rate alone one direction is equal to the etch rate along an orthogonal direction), or an anisotropic etch (i.e., the etch rate along one direction is less than the etch rate alone an orthogonal direction), or variants thereof.

In some cases, an anisotropic etch removes the majority of the volume of the well. Any suitable percentage of the well volume can be removed including about 60%, about 70%, about 80%, about 90%, or about 95%. In some cases, at least about 60%, at least about 70%, at least about 80%, at least about 90%, or at least about 95% of the material is removed in an anisotropic etch. In some cases, at most about 60%, at most about 70%, at most about 80%, at most about 90%, or at most about 95% of the material is removed in an anisotropic etch. In some embodiments, the anisotropic etch does not remove silicon dioxide material all of the way down to the semiconductor substrate. An isotropic etch removes the silicon dioxide material all of the way down to the semiconductor substrate in some instances.

In some cases, the wells are etched using a photo-lithographic operation to define the wells followed by a hybrid dry-wet etch. The photo-lithographic operation can comprise coating the silicon dioxide with a photo-resist and exposing the photo-resist to electromagnetic radiation through a mask (or reticle) having a pattern that defines the wells. In some instances, the hybrid dry-wet etch comprises: (a) dry etching to remove the bulk of the silicon dioxide in the well regions defined in the photoresist by the photo-lithographic operation; (b) cleaning the biochip; and (c) wet etching to remove the remaining silicon dioxide from the substrate in the well regions.

The biochip can be cleaned with the aid of a plasma etching chemistry, or exposure to an oxidizing agent, such as, for example, H2O2, O2, or O3. The cleaning can comprise removing residual polymer, removing material that can block the wet etch, or a combination thereof. In some instances, the cleaning is plasma cleaning. The cleaning operation can proceed for any suitable period of time (e.g., 15 to 20 seconds). In an example, the cleaning can be performed for 20 seconds with an Applied Materials eMAx-CT machine with settings of 100 mT, 200 W, 20 G, 20 O2.

The dry etch can be an anisotropic etch that etches vertically (e.g., toward the semiconductor substrate) but not laterally (e.g., parallel to the semiconductor substrate). In some instances, the dry etch comprises etching with a fluorine based etchant such as CF4, CHF3, C2F6, C3 F6, or any combination thereof. In one instance, the etching is performed for 400 seconds with an Applied Materials eMax-CT machine having settings of 100 mT, 1000 W, 20 G, and 50 CF4.

The wet etch can be an isotropic etch that removes material in all directions. In some instances, the wet etch undercuts the photo-resist. Undercutting the photo-resist can make the photo-resist easier to remove in a later operation (e.g., photo-resist "lift off"). In an embodiment, the wet etch is buffered oxide etch (BOE). In some cases, the wet oxide etches are performed at room temperature with a hydrofluoric acid base that can be buffered (e.g., with ammonium fluoride) to slow down the etch rate. Etch rate can be dependent on the film being etched and specific concentrations of HF and/or NH4F. The etch time needed to completely remove an oxide layer is typically determined empirically. In one example, the etch is performed at 22° C. with 15:1 BOE (buffered oxide etch).

The silicon dioxide layer can be etched to an underlying material layer. For example, with reference to FIG. 13, the silicon dioxide layer is etched until the titanium nitride layer.

In an aspect, a method for preparing a biochip comprises etching wells into a silicon dioxide layer coated onto a semiconductor substrate using (a) a photo-lithographic operation to define the wells; (b) a dry etch to remove the bulk of the silicon dioxide in the well regions defined by the photo-lithographic operation; and (c) a wet etch to remove the remaining silicon dioxide from the substrate in the well regions. In some cases, the method further comprises removing residual polymer, removing material that can block the wet etch, or a combination thereof. The method can include a plasma cleaning operation.

As shown in FIG. 13, the photo-resist is not removed from the silicon dioxide following the photo-lithographic operation or the hybrid wet-dry etch in some cases. Leaving the photo-resist can be used to direct metal only into the wells and not onto the upper surface of the silicon dioxide in later operations. In some cases, the semiconductor substrate is coated with a metal (e.g., aluminum in FIG. 13) and the wet etch does not remove components that protect the metal from corrosion (e.g., titanium nitride (TiN) in FIG. 13). In some cases, however, the photoresist layer can be removed, with a wet chemistry such as SPM (sulfuric/peroxide mixture) or an organic solvent. In other embodiments, the photoresist layer may be removed with an oxygen plasma.

Electrode Metallization

Biochips described herein can be used to detect molecules and/or sequence nucleic acid molecules with aid of a nanopore and electrical detection. Electrical detection can be performed with aid of an electrode in the well and a counter-electrode located outside the well. Provided herein are methods for creating electrodes, such as metal electrodes. The electrode can be reversibly consumed during detection, not consumed during detection, or not appreciably consumed during detection.

An example of an electrode that may be reversibly consumed during molecular detection is silver. An example of an electrode that may not be appreciably consumed during detection is platinum.

An electrode can be formed adjacent to a substrate with the aid of various deposition techniques. For instance, an electrode can be formed with the aid of electroplating. As another example, an electrode can be formed with the aid of a vapor deposition techniques, such as, for example, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD) and physical vapor deposition (e.g., sputter deposition, evaporative deposition).

Figure 14:
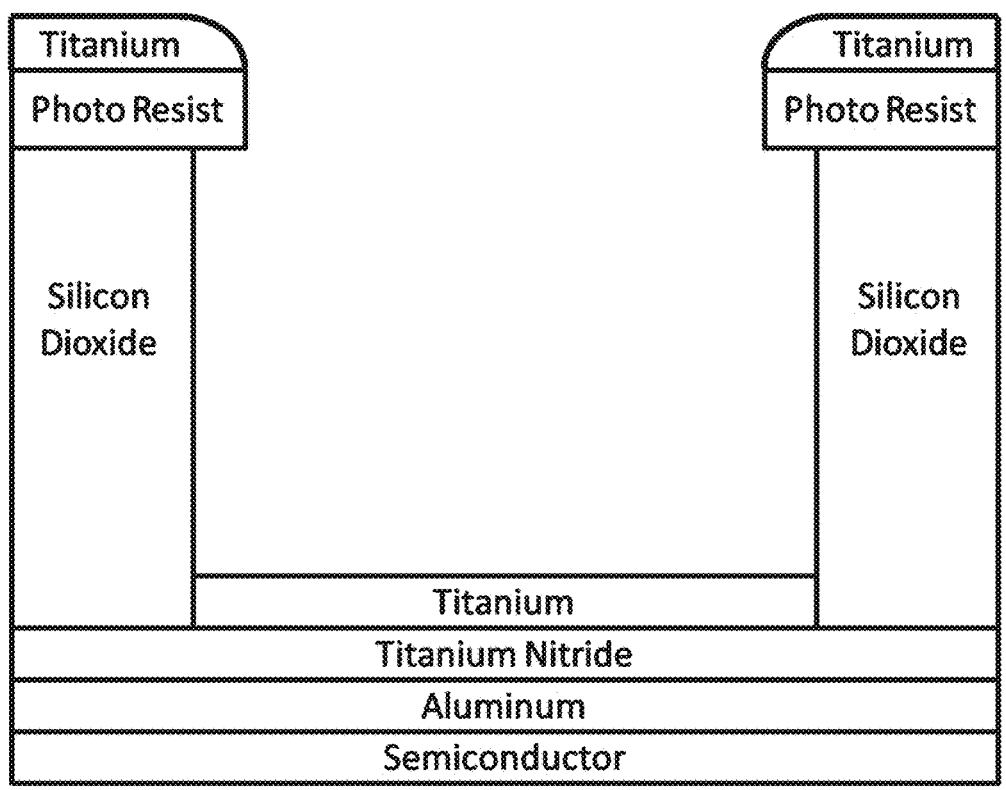
FIG. 14 shows deposition of a titanium adhesion layer.
Figure 15:
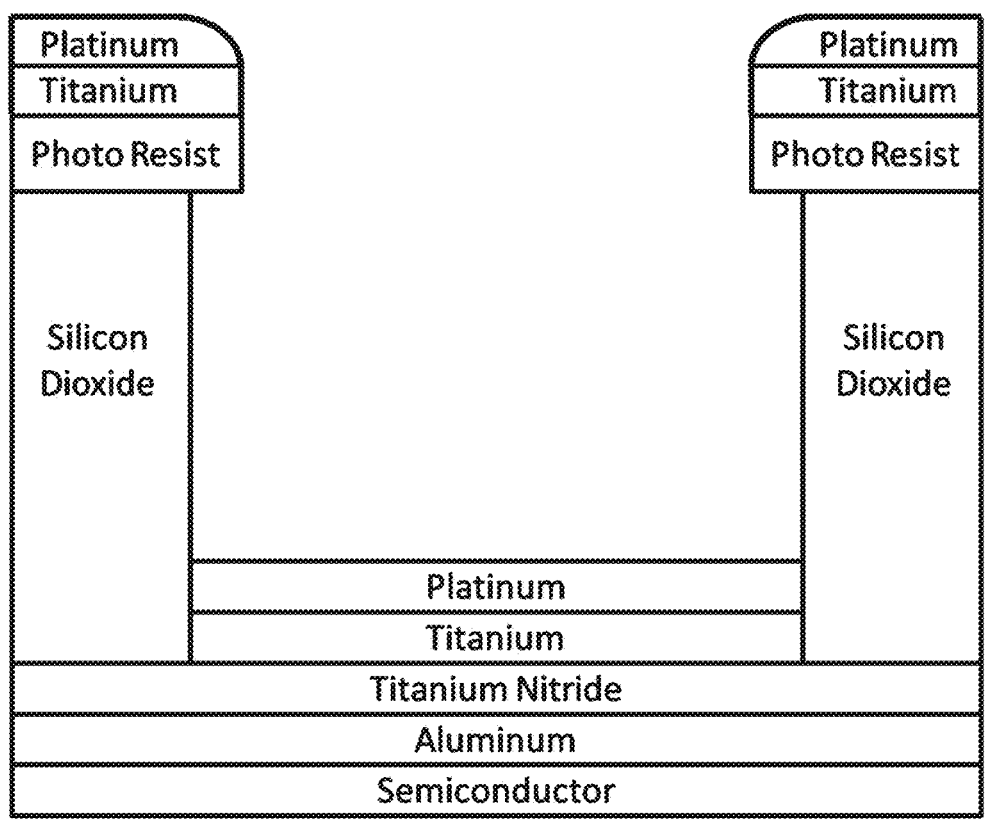
FIG. 15 shows deposition of a titanium Nitride protective layer with Platinum protective layer or alternately Platinum serving as the electrode.
Figure 16:
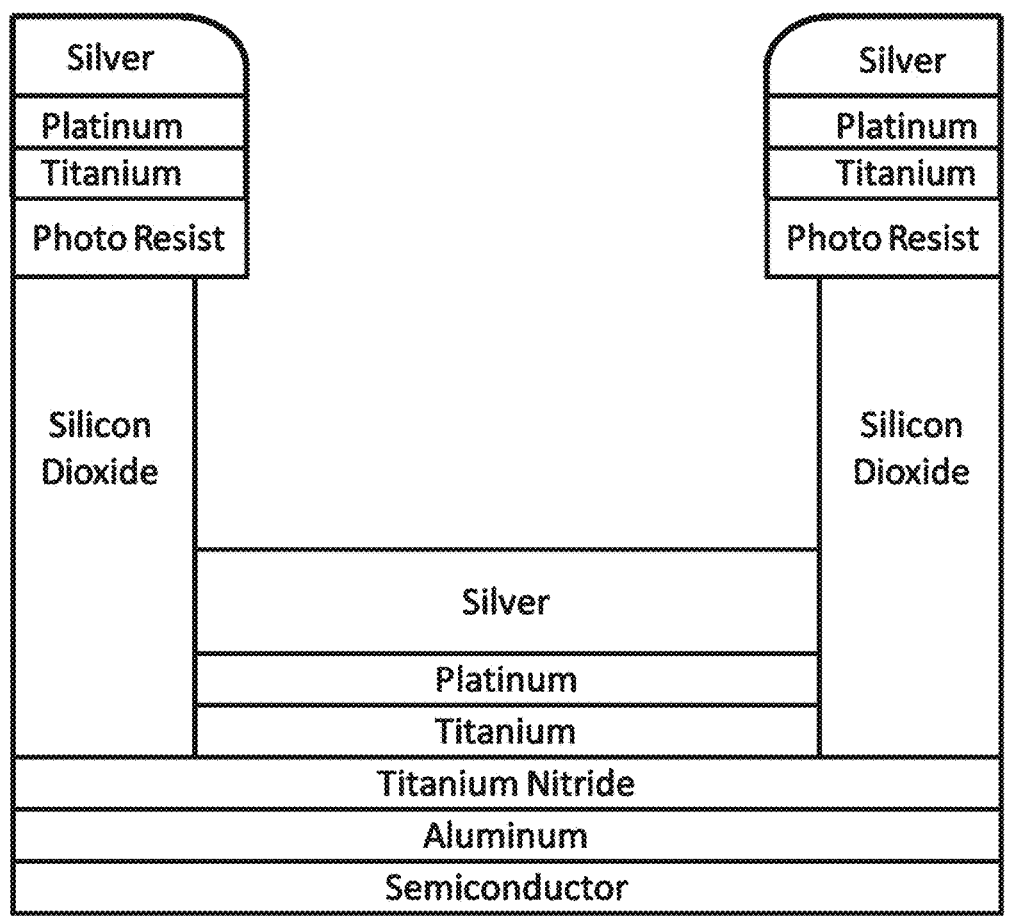
FIG. 16 shows deposition of silver electrode material.

In an aspect, a method for preparing a biochip comprises (a) providing a semiconductor substrate coated with a layer of silicon dioxide, where a well is etched into the silicon dioxide (e.g., as shown in FIG. 13); (b) depositing a protective layer onto the well surface (e.g., Titanium Nitride or platinum as shown in FIG. 15); and (c) depositing the electrode material onto the well surface (e.g., silver as shown in FIG. 16). The method can further comprise depositing a film of adhesion material onto the well surface to provide for adhesion and electrical conductivity of a metal layer to a layer below the metal layer. The adhesion material can comprise titanium, tantalum, titanium nitride (TiN), chromium, or any combination thereof. With reference to FIG. 14, an adhesion material comprising titanium is deposited adjacent to the titanium nitride layer, such as, for example, by electroplating, or vapor deposition (e.g., chemical vapor deposition). In some cases, a single layer of metal replaces two or more layers (e.g., a single metal layer is both the adhesion layer and protective layer).

In some cases, the protective layer comprises a corrosive resistant metal (e.g., platinum, gold). Without limitation, the protective layer can (i) provide electrical connectivity to an underlying conductor (e.g., to aluminum in FIG. 14, or titanium nitride), (ii) protect the underlying conductor from attack by a reactive solution (e.g., a corrosive solution such as sodium chloride in water), (iii) provide an electron source and/or sink so that an electrode material is not consumed in redox reactions (e.g., platinum can act as the source and/or sink when the electrode comprises silver), or (iv) any combination thereof.

The various layers of metal (e.g., adhesion layer, protective layer, electrode material, etc.) can be deposited by any suitable technique, such as sputtering, deposition, electroplating, or a combination thereof. In some instances, the electrode material is deposited by sputtering, such as, for example, magnetron sputtering.

The electrodes are capable of making any suitable measurement as required for operation of the biochip. In some cases, the electrode material makes electrical measurements of analytes in the wells. The analytes can comprise nucleic acids, amino acids, proteins, tag molecules, or any combination thereof. The electrical measurements can reversible redox reactions. In some embodiments, a sufficient volume of the electrode material is deposited into the well to provide for detection of redox reactions involving analytes in the wells.

Lift-Off Procedure

There can be one or more layers of metal deposited onto the photo-resist following electrode metallization as shown in FIG. 16. In some instances, the metal deposited onto the photo-resist is removed from the biochip while the metal deposited in the wells remains in the wells. Leaving the photo-resist following creation of the wells (e.g., as shown in FIG. 13) can be advantageous for achieving metal removal from only the surface of the biochip and not the wells.

In some situations, following formation of a well and an electrode, the photoresist may be omitted and metal outside of the electrode well can be removed with the aid of a chemical mechanical polishing and subsequent wet or reactive ion etching (RIE) etch if desired. In an example, CMP is used to remove the electrode metal stack on the surface of the chip while it remains in the well (damascene process). In another example, the photoresist and any overlying layer is removed using acetone or another resist solvent (liftoff process).

Silanization of the Biochip Surface

Following formation of a well and electrode within the well, the silicon dioxide layer can be treated to render the silicon dioxide layer suitable for forming a membrane in or adjacent to the well. In some cases, a hydrophobic membrane, such as, for example, a bilayer (e.g., lipid bilayer), is formed over the well. The membrane can isolate the etched well from an overlying liquid, such as, for example, with a resistivity of at least about 10 gigaohms. As described herein, silanization of the silicon dioxide surface (e.g., to make the surface hydrophobic) makes the surface suitable for formation of a membrane.

A method for stabilizing a membrane to a semiconductor interface comprises silanizing a semiconductor surface such that a membrane is capable of adhering to the silanized surface and separating a first fluid (e.g., on the cis side of the membrane) from a second fluid (e.g., on the trans side of the membrane) with a resistivity of, for example, at least about 10 gigaohms.

Figure 17:
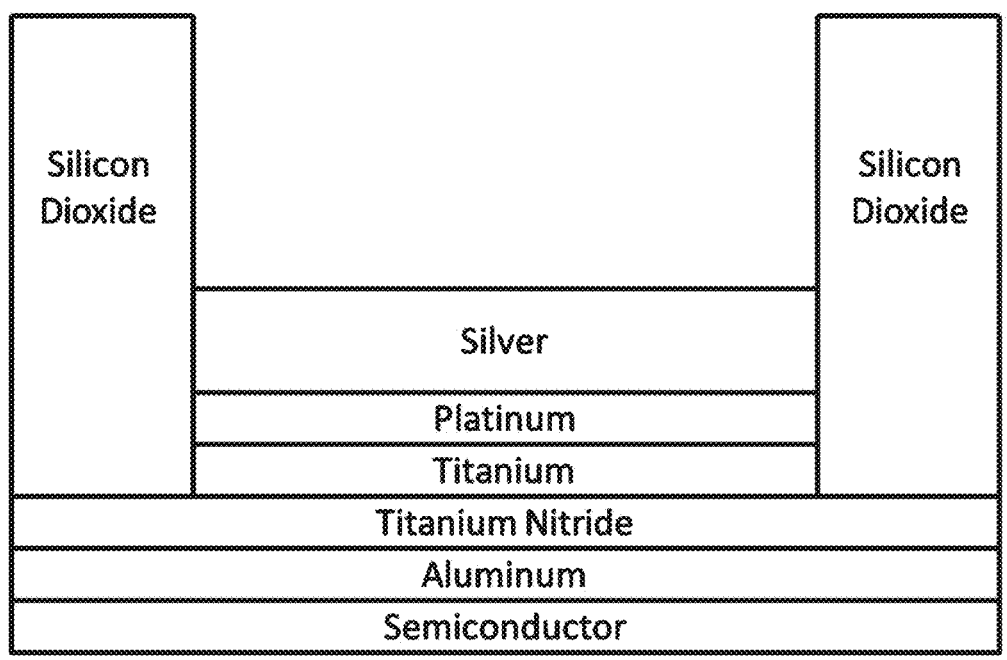
FIG. 17 shows lift off of the photo-resist and materials disposed thereupon.
Figure 18:
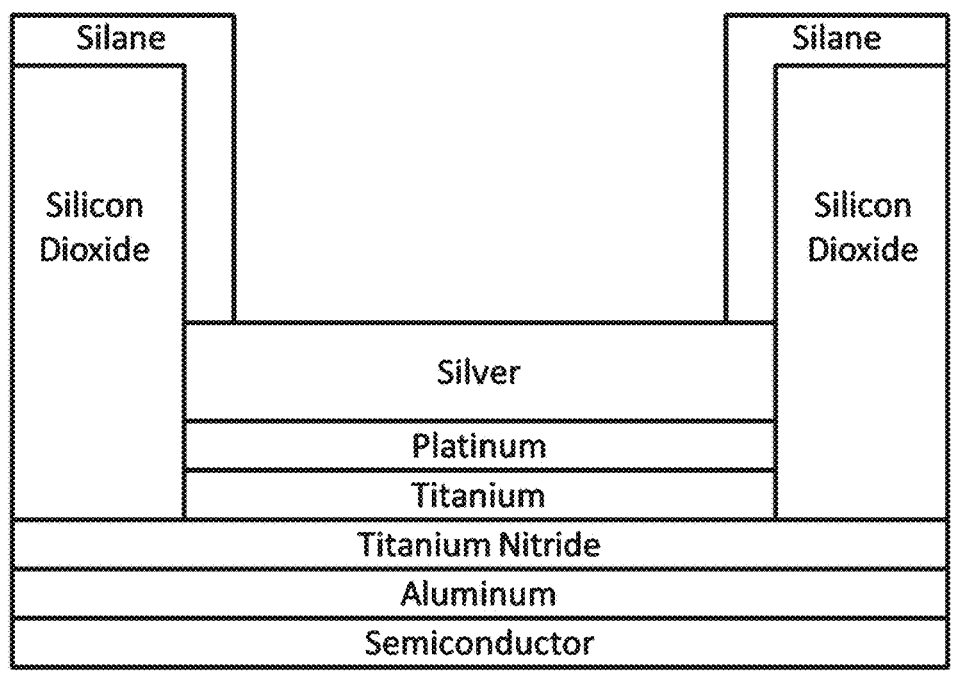
FIG. 18 shows silanization of the silicon dioxide.

A method for preparing a biochip can comprise: (a) providing a packaged biochip or biochip precursor having a surface that comprises silicon dioxide and/or metal (e.g., as shown in FIG. 17); and (b) silanizing the surface (e.g., as shown in FIG. 18) using, for example, an organofunctional alkoxysilane molecule. In some cases, the organofunctional alkoxysilane molecule is dimethylchloro-octodecyl-silane, dimethylmethoxy-octodecyl-silane, methyldichloro-octodecyl-silane, trichloro-octodecyl-silane, trimethyl-octodecyl-silane, triethyl-octodecyl-silane or any combination thereof.

The organofunctional alkoxysilane molecule can cover the silicon dioxide surfaces (as shown in FIG. 18). The silane layer can be one molecule in thickness (FIG. 18).

Following silanization, the method can further comprise removing residual silane from the substrate with a rinsing protocol. An example rinsing protocol is a 5 second rinse with decane, acetone, ethanol, water, and ethanol followed by air drying and heating at 97° C. for 30 minutes. The rinsing protocol can also used to clean the chip prior to the application of the silane layer.

Figure 21:
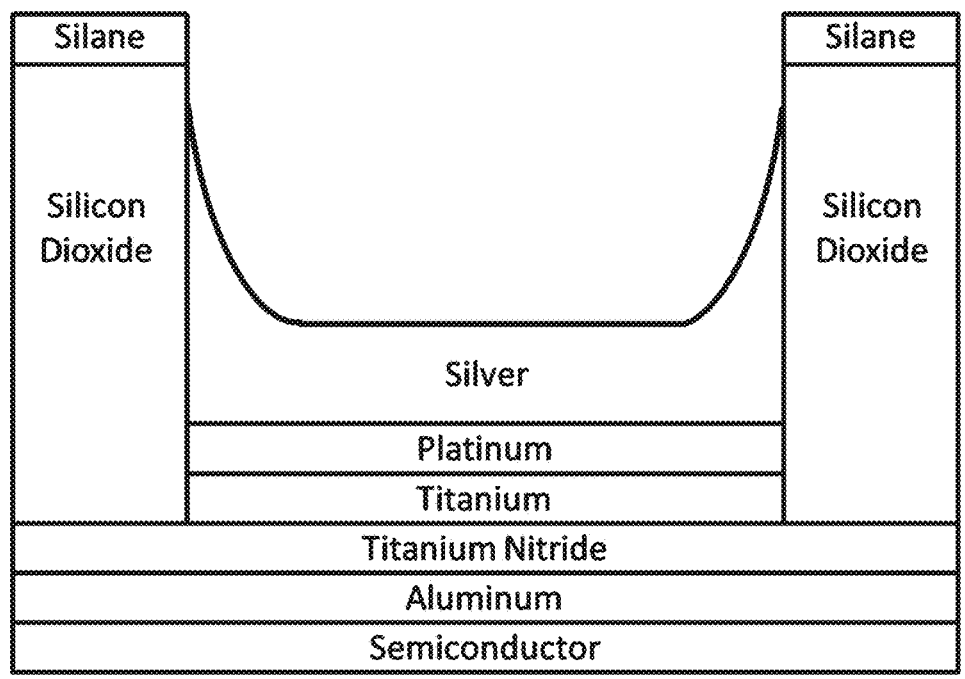
FIG. 21 shows a biochip where the silver electrode comes up on the side walls of the well.

FIG. 21 shows that the silver and protective metal underneath can sputter onto the side walls of the wells and thus the silanization may not come down into the well. In some instances, three fourths or more of the side walls of the wells are covered with silver and the protective layer underneath.

Formation of Bilayers

Described herein are methods for creating lipid bilayers and nanopores on an array of electrodes (e.g., individually controlled) that make up a semiconductor nanopore sensor chip. The chip can be used for determining a polymer sequence, such as nucleic acid sequence, or the presence of any tagged molecule.

Techniques for forming lipid bilayers over an array of electrodes on a semiconductor sensor chip are described herein. In an embodiment, liquids containing lipid molecules are inserted to the surface of the chip. The liquids can be separated by bubbles. The lipid molecules can be distributed on the surface and the bubbles thin out the lipids to spontaneously form a lipid bilayer over each of the electrodes. Additional electrical stimulus may be applied to the electrodes to facilitate the bilayer formation. Solutions containing nanopore protein may be further applied on top of the deposited lipids. More bubbles may be rolled across the chip to facilitate the nanopore insertion into the bilayers. These techniques may occur with or without flow cells. In some cases, additional stimulus can be applied to induce bilayer or pore creation. Such stimulus can include pressure, sonication, and/or sound pulses. A stimulus may include any combination of buffers (pH range of about 5.0 to about 8.5), ionic solutions (e.g., NaCl, KCl; about 75 mM to about 1 M), bubbles, chemicals (e.g., hexane, decane, tridecane, etc.), physical movement, electrical stimulus or electrical stimulus pulses, pressure or pressure pulses, temperature or temperature pulses, sonication pulses, and or sound pulses to the sensor chip.

Figure 22:
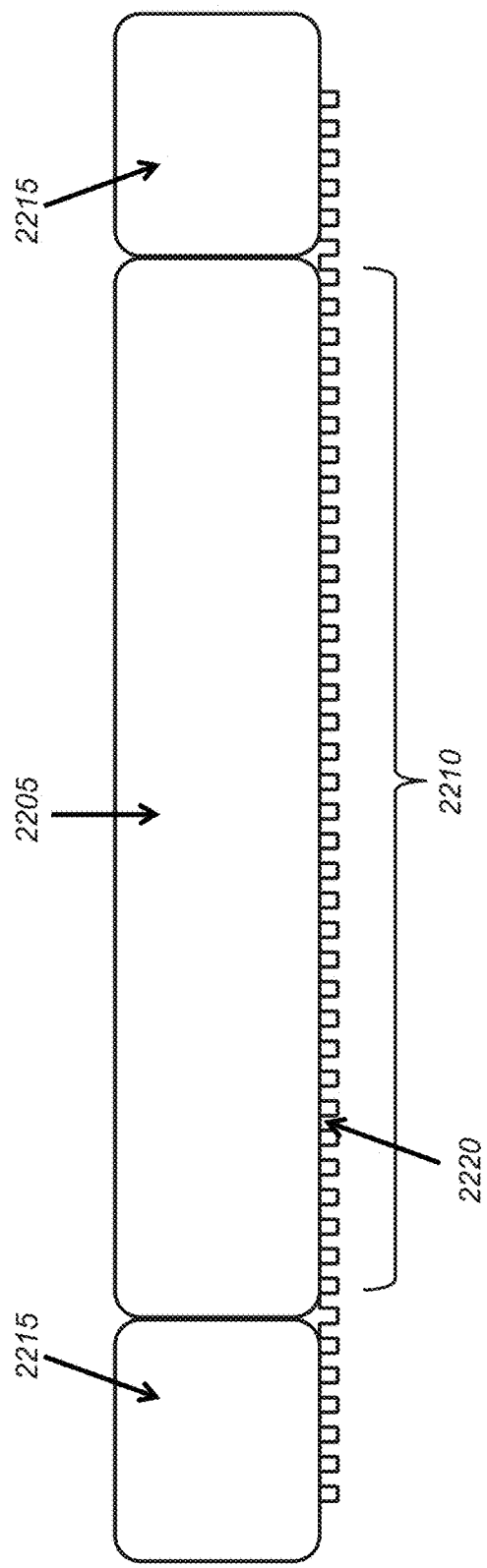
FIG. 22 shows a large bubble held adjacent to a plurality of electrodes.
Figure 30:
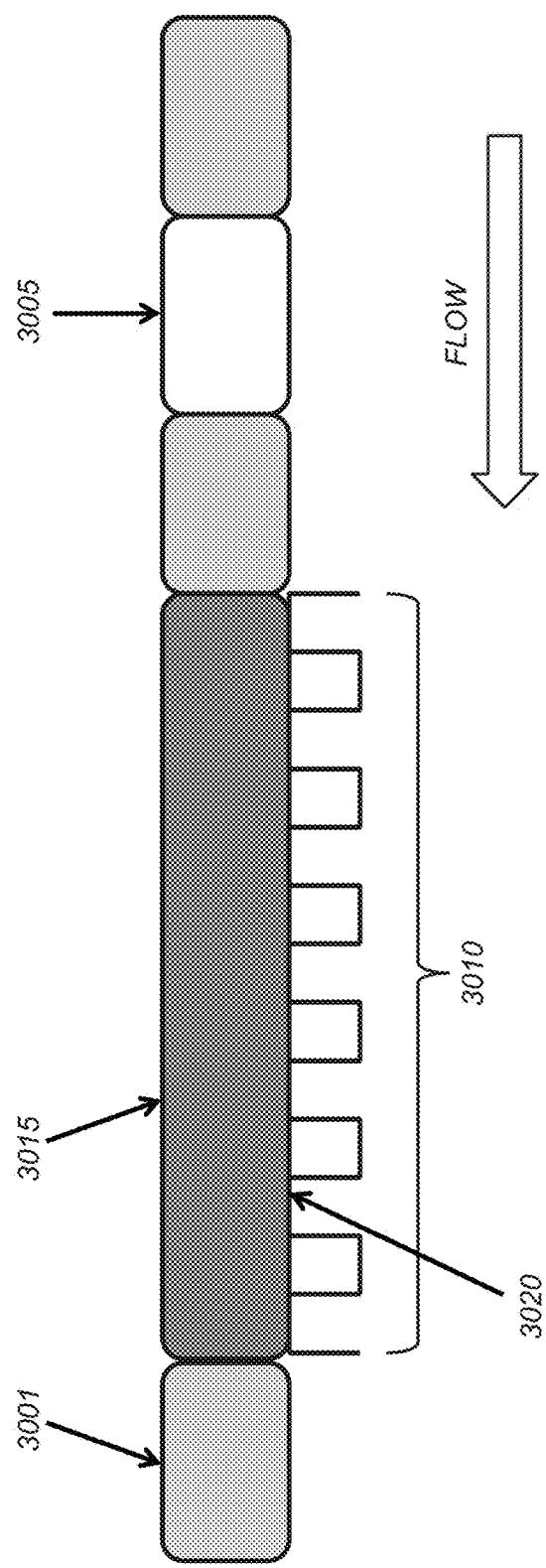
FIG. 30 is an illustration of the flow of various solutions and/or bubbles over the wells of a sensor chip. The direction of flow is indicated by the block arrow in the lower right corner of the diagram. In this figure, the first rectangle representing ionic solution (3001; divot patterned rectangle) has already flowed over the wells (3010), the lipid solution (3015; cross-hatched rectangle) is on the chip (and in this depiction covers all of the wells), and the second and third rectangles representing ionic solution, as well as the bubble (3005; clear rectangle) have not yet been flowed onto the chip. The size of the rectangles is not representative of the amount of the fluid or size of the bubble. The ionic solution-bubble-ionic solution sequence may be repeated several times in order to increase the bilayer coverage, decrease the non-bilayer coverage, e.g., multi-layer stacks of lipids on the wells, and/or reestablish the bilayer after a pop test. The lipid bilayer will form at the interface (3020) of the wells (shown) or substantially planar electrodes (not shown) once the method described herein is performed.

As shown in FIG. 22, the bubble 2205 can be large and held adjacent to a plurality of wells 2210, each well 2210 containing an electrode. The bubble can displace lipid from the region adjacent to the electrodes to produce (a) lipid bilayer(s) that cover the electrode(s). In some cases, the edge of the bubble is contacted with a lipid solution 2215 and some of the lipid solution diffuses under 2220 the bubble 2205 to form (a) lipid bilayer(s) that cover the wells 2210 and the electrode(s). The bubble can be a gas (or vapor) bubble. The bubble can include a single gas or a combination of gases, such as, e.g., air, oxygen, nitrogen, argon, helium, hydrogen, or carbon dioxide. FIG. 30 also provides another illustration of the bilayer formation methods as provided for herein.

The bubble can cover and/or be adjacent to any suitable number of electrodes. In some cases, the bubble is adjacent to about 100, about 1000, about 10000, about 100000, about 1000000, or about 10000000 electrodes. In some instances, the bubble is adjacent to at least about 100, at least about 1000, at least about 10000, at least about 100000, at least about 1000000, or at least about 10000000 electrodes.

The bubble can remain adjacent to the electrodes for any suitable period of time (e.g., long enough to form lipid bilayers). In some cases, the bubble is held adjacent to the electrodes for between about 10 ms to about 10 minutes, e.g., 0.5 second (s), about 1 s, about 3 s, about 5 s, about 10 s, about 20 s, about 30 s, about 45 s, about 60 s, about 1.5 minutes (min), about 2 min, about 3 min, about 4 min, about 5 min, or about 10 min. In some cases, the bubble is held adjacent to the electrodes for at least about 0.5 second (s), at least about 1 s, at least about 3 s, at least about 5 s, at least about 10 s, at least about 20 s, at least about 30 s, at least about 45 s, at least about 60 s, at least about 1.5 minutes (min), at least about 2 min, at least about 3 min, at least about 4 min, at least about 5 min, or at least about 10 min. In some cases, the bubble is held adjacent to the electrodes for at most about 0.5 second (s), at most about 1 s, at most about 3 s, at most about 5 s, at most about 10 s, at most about 20 s, at most about 30 s, at most about 45 s, at most about 60 s, at most about 1.5 minutes (min), at most about 2 min, at most about 3 min, at most about 4 min, at most about 5 min, or at most about 10 min. In some instances, the bubble is held adjacent to the electrodes for between about 1 s and about 10 min, between about 10 s and about 5 min, or between about 30 s and about 3 min.

Figure 24:
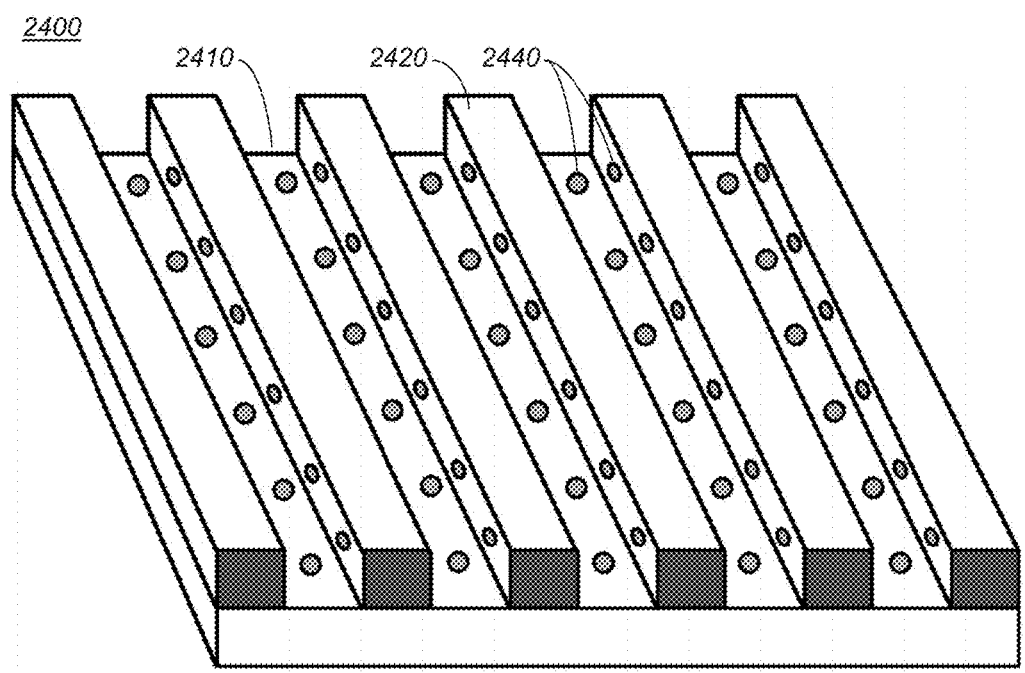
FIG. 24 shows an example of a semiconductor sensor chip.

In an aspect, a method for forming a lipid bilayer for use in a nanopore sensing device comprises providing a primed chip comprising a fluid flow path in fluid communication with a plurality of sensing electrodes, and flowing a lipid solution into the fluid flow path and flowing a bubble onto the fluid flow path, thereby forming a lipid bilayer adjacent to each of the sensing electrodes. As used herein, a primed chip is a chip that has had an initial flow of a KCl or an ionic solution over the chip and filling all the wells or channels. FIG. 7 shows an example of a device having two fluid flow paths and FIG. 24 shows an example of a device having 5 fluid flow paths. In some embodiments, the bubble spans the plurality of sensing electrodes and is adjacent to the sensing electrodes for at least about 1 second. The bubble can be adjacent to the sensing electrodes or wells containing sensing electrodes for at least between about 10 ms to about 10 minutes, e.g., 5 seconds, at least about 10 seconds, at least about 30 seconds and/or at most about 1 minute, 2 minutes, 3 minutes, 4 minutes, 5 minutes or 10 minutes. In some cases, a nanopore is inserted into the lipid bilayers adjacent to each of the sensing electrodes.

In an aspect, a method for forming a lipid bilayer for use in a nanopore sensing device comprises providing a primed chip comprising a fluid flow path in fluid communication with a plurality of sensing electrodes, flowing a bubble onto the fluid flow path, where the bubble spans the plurality of sensing electrodes and contacting the periphery of the bubble with a lipid. The lipid can diffuse under the bubble and onto the fluid flow path (e.g., thereby forming a lipid bilayer adjacent to each of the sensing electrodes). In some cases, the method further comprises inserting a nanopore into the lipid bilayers adjacent to each of the sensing electrodes.

The bubble can be contacted with the lipid for any suitable period of time (e.g., long enough to form lipid bilayers). In some cases, the bubble is contacted with the lipid for about 0.5 second (s), about 1 s, about 3 s, about 5 s, about 10 s, about 20 s, about 30 s, about 45 s, about 60 s, about 1.5 minutes (min), about 2 min, about 3 min, about 4 min, about 5 min, or about 10 min. In some cases, the contacted with the lipid for at least about 0.5 second (s), at least about 1 s, at least about 3 s, at least about 5 s, at least about 10 s, at least about 20 s, at least about 30 s, at least about 45 s, at least about 60 s, at least about 1.5 minutes (min), at least about 2 min, at least about 3 min, at least about 4 min, at least about 5 min, or at least about 10 min. In some cases, the bubble is contacted with the lipid for at most about 0.5 second (s), at most about 1 s, at most about 3 s, at most about 5 s, at most about 10 s, at most about 20 s, at most about 30 s, at most about 45 s, at most about 60 s, at most about 1.5 minutes (min), at most about 2 min, at most about 3 min, at most about 4 min, at most about 5 min, or at most about 10 min. In some instances, the bubble is contacted with the lipid for between about 1 s and about 10 min, between about 10 s and about 5 min, or between about 30 s and about 3 min.

The method can form a lipid bilayer over any proportion of the electrodes. In some cases, a lipid bilayer is formed over at least about 10%, at least about 20%, at least about 30%, at least about 40%, at least about 50%, at least about 60%, at least about 70%, at least about 80%, or at least about 90% of the sensing electrodes. In some examples, a lipid bilayer is formed over about 10%, about 20%, about 30%, about 40%, about 50%, about 60%, about 70%, about 80%, or about 90%, or about 100% of the sensing electrodes.

The bilayers can provide an electrical resistance between a solution on the cis-side of the lipid bilayer and a solution on the trans-side of the bilayer. In some cases, the resistance is about 100 mega-ohm (MΩ), about 500 MΩ, about 1 giga-ohm (GΩ), about 10 GΩ, or about 100 GΩ. In some cases, the resistance is at least about 100 mega-ohm (MΩ), at least about 500 MΩ, at least about 1 giga-ohm (GΩ), at least about 10 GΩ, or at least about 100 GΩ. In some embodiments, the resistance is about 1 tera-ohm (TΩ).

Inserting the nanopore can comprise applying an electrical stimulus (e.g., voltage pulse or current pulse) through the electrode to facilitate the insertion of the nanopore in the lipid bilayer. As an alternative, or in addition to, a nanopore can be inserted by applying one or more other stimuli, such as, for example, a pressure pulse, or any combination of buffers (pH range of about 5.0 to about 8.5), ionic solutions (e.g., NaCl, KCl; about 75 mM to about 1 M), bubbles, chemicals (e.g., hexane, decane, tridecane, etc.), physical movement, electrical stimulus or electrical stimulus pulses, pressure or pressure pulses, temperature or temperature pulses, sonication pulses, and or sound pulses to the sensor chip. The nanopore can be any nanopore (e.g., a protein nanopore). In some embodiments, the nanopore is *Mycobacterium smegmatis* porin A (MspA), alpha-hemolysin, any protein having at least 70% homology to at least one of smegmatis porin A (MspA) or alpha-hemolysin, or any combination thereof.

In some instances, the resistance across the bilayer is reduced upon insertion of a nanopore. The bilayers after nanopore insertion can provide an electrical resistance between a solution on the cis-side of the lipid bilayer and a solution on the trans-side of the bilayer. In some cases, the resistance after nanopore insertion is about 1 mega-ohm (MΩ), about 10 MΩ, about 100 MΩ, about 500 MΩ, about 1 giga-ohm (GΩ). In some cases, the resistance after nanopore insertion is at most about 1 mega-ohm (MΩ), at most about 10 MΩ, at most about 100 MΩ, at most about 100 MΩ, at most about 500 MΩ, at most about 1 giga-ohm (GΩ).

The lipid can be any suitable lipid or a mixture of lipids. In some cases, the lipid is dissolved in an organic solvent. In some embodiments, lipid is selected from the group consisting of diphytanoylphosphatidylcholine (DPhPC), 1,2-diphytanoyl-sn-glycero-3-phosphocholine, Lysophosphatidylcholine (LPC), 1,2-Di-O-Phytanyl-sn-Glycero-3-phosphocholine (DoPhPC), palmitoyl-oleoyl-phosphatidyl-choline (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy(polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy (polyethylene glycol)-1000]; 1,2-dipalmitoyl-sn-glycero-3-phosphoethanolamine-N-[methoxy(polyethylene glycol)-2000]; 1,2-dioleoyl-sn-glycero-3-phosphoethanolamine-N-lactosyl; GM1 Ganglioside, or any combination thereof.

In an aspect, a method for forming a lipid bilayer for use in a nanopore sensor, comprises directing a buffer solution in flow channel comprising an electrode (or well containing an electrode) having a material layer thereon. The buffer solution can be electrically conductive, and the material layer can comprise one or more lipids. Next, the buffer solution can be brought in contact with the material layer, and one or more voltages can be applied to the electrodes to encourage bilayer formation. Subsequently a current through the electrodes can be measured to determine if at least a portion of the material layer has covered and sealed the electrodes and/or formed a bilayer over all or a portion of the electrode. The applied voltage may be sufficient to break the bilayer seal over the electrode and cause short circuit current flow. Based on a determination as to whether at least the portion of the material layer has covered and sealed the electrodes and/or formed a bilayer over all or a portion of the electrode, a stimulus may be applied simultaneously to all of the electrodes, groups of the electrodes, or individual electrodes to induce at least the portion of the material layer to form the lipid bilayer adjacent to the electrode.

In some embodiments, the stimulus comprises at least one of a liquid flow over the surface of the electrode array, the sequential flow of one or more different liquids over the surface of the array, the sequential flow of any combination of one or more different liquids and bubbles over the surface of the array, an electrical pulse, sonication pulse, pressure pulse, or sound pulse. In some embodiments, the stimulus comprises any combination of buffers (pH range of about 5.0 to about 8.5), ionic solutions (e.g., NaCl, KCl; about 75 mM to about 1 M), bubbles, chemicals (e.g., hexane, decane, tridecane, etc.), physical movement, electrical stimulus or electrical stimulus pulses, pressure or pressure pulses, temperature or temperature pulses, sonication pulses, and or sound pulses. In some cases, the material layer comprises at least two types of lipids. In some examples, the stimulus comprises the sequential flow of one or more liquids and bubbles over the surface of the array.

In an aspect, an automated method for creating a lipid bilayer on top of each one of multiple electrodes that make up an array of individually controlled electrodes and a method to insert a single pore into each bilayer atop each electrode in an array of individually controlled electrodes on a semiconductor sensor is described. By applying an appropriate external stimulus (e.g., electrical stimulus, pressure stimulus, sonication, or sound) to a lipid layer in close proximity to an electrode on an essentially planar surface, a bilayer can be induced to form over the electrode in an array of electrodes. Additionally, by applying an appropriate external stimulus (e.g., including electrical stimulus, pressure stimulus, sonication, or sound) to an individual electrode to the entire sensor chip that has lipid bilayers on one or more electrodes and that are covered with a solution containing nanopore proteins, a pore may be induced to insert into the bilayer. The result is that a bilayer is created automatically, without manual intervention, over multiple electrodes in an array of individually controlled electrodes in response to a stimulus and in a deterministic manner. In some cases, a single nanopore can be inserted into multiple electrode/bilayers in response to a stimulus and in a deterministic manner and therefore create a highly parallel array of individually controlled, electrical nanopore sensors. These arrays of individually controlled nanopore sensors may be created on an essentially planar semiconductor surface and that within the semiconductor material are created a portion or all of the circuitry needed to operate and control the individual electrodes.

In addition to the above approaches of creating bilayers and pores, the present disclosure provides methods to create bilayers and pores on arrays of individually controlled electrical/nanopore sensors that are cost effective and relatively simple and include 1) activating lipid or lipid-porin protein mixes already on the sensor (pre-applied) and causing spontaneous bilayer creation or bilayer-pore creation, 2) activating lipid or lipid-porin protein mixes already on the sensor (pre-applied) and directly creating bilayers and or pores via electrical stimulation at the electrodes or stimulation to the system to create bilayers and or pores 3) activating lipid or lipid-porin protein mixes already on the sensor (pre-applied) and directly creating bilayers and or pores via contacting a bubble to or running a bubble across the surface of a sensor chip, 4) activating lipid or lipid-porin protein mixes already on the sensor (pre-applied) and distributing, and thinning the mixture on the surface of a sensor array using a bubble that prepares the surface for subsequent electrical stimulation at the electrodes or stimulation to the system to create bilayers and or pores, 5) using a bubble to apply, distribute and thin a lipid mixture on the surface of a sensor array so that bilayers are created over multiple independent electrodes in an array, 6) using a bubble to apply, distribute and thin a lipid mixture and prepare the surface for subsequent electrical stimulation at the electrodes or stimulation to the system to create bilayers over multiple electrodes, 7) using a bubble to apply, distribute and thin a porin protein mixture on the surface of a sensor array prepared with a lipid mixture so that pores are inserted over multiple independent electrodes in an array, 8) using a bubble to apply, distribute and thin a porin protein mixture and prepare the surface for subsequent electrical stimulation at the electrodes or stimulation to the system to create a single pore over multiple electrodes in an array, 9) using an electrical stimulus to create a bilayer over the surface of an electrode that does not require the generation or application of a bubble over the surface of an electrode, 10) using sonication or pressure stimulus applied to one or more electrodes, or to the entire sensor chip, to create a bilayer and/or pore over the surface of an electrode or multiple electrodes, 11) increasing the density of electrodes on a semiconductor array of electrodes for nanopore electrical sensing that is compatible with the methods for establishing bilayers and pores described above, 12) using a setup in which no flow cell or an open single sensor chip containing an array of multiple electrode-nanopore sensors can support the methods above or elsewhere herein, or a single flow cell on a single sensor chip containing an array of multiple electrode-nanopore sensors can support the methods above or elsewhere herein, or multiple flow cells on a single sensor chip containing an array of multiple electrode-nanopore sensors can support the methods above or elsewhere herein, 13) varying a pressure of the liquid or bubble to improve successful bilayer or pore creation, and 14) varying a temperature of the sensor chip and liquid to improve bilayer or pore creation.

The present disclosure provides various approaches to create lipid bilayer and to insert a pore in the bilayer. In an embodiment, a semiconductor chip with multiple electrodes is presented. A liquid lipid solution is applied to the silanized prepared surface of the chip. The liquid lipid solution may be a solution of an organic solvent, e.g., decane, hexane, tridecane, etc., and lipid molecules, such as diphytanoyl-phosphatidylcholine (DPhPC) and/or any of the lipids noted above. The solution may be applied on the surface by flowing, pouring, spraying, and/or squeegee. The solution is dried down on the surface. The solution may be substantially or completely dried so that only powder form of DPhPC molecules are left. As an alternative, the solution may be dried down to a sticky state. As such, the surface of the chip can be functionalized by the pre-applied lipid molecules in a powder form or a sticky solution form. The chip is sealed and may be handled and shipped.

The semiconductor chip may contain a cover and the cover can allow the user to pump in and pump out (or otherwise direct the movement of) liquid across the chip. In some examples, the user applies a buffer liquid (or solution), such as salt water, into the chip to activate lipid molecules, which may be in a dried or substantially dried state. Once the lipid molecules contact with the buffer solution, the lipid molecules are hydrated. The pressure of the incoming buffer liquid may facilitate the formation of a lipid bilayer on top of each electrode surface. The formation of the lipid bilayer may be spontaneous.

In some situations, the semiconductor chip may not contain a cover and the user applies a buffer liquid (or solution), such as salt water, onto the chip surface using a pipette or other fluid transfer and/or movement device (or instrument) to activate lipid molecules. Once the lipid molecules contact with the buffer solution, the lipid molecules are hydrated. The pressure of the incoming buffer liquid may facilitate the formation of a lipid bilayer on top of each electrode surface.

In situations in which the semiconductor chip contains a cover, after the buffer liquid is applied into the chip, a bubble can be pumped in, and behind the bubble there is more buffer solution than in front of the bubble. The bubble sweeps across the chip and smoothes/thins out the newly hydrated pre-deposited lipid mixture and causes the lipid molecules to sweep across the surface. After the bubble flows through, a lipid bilayer may be formed on top of each electrode surface.

In some cases, after the bubble is applied and sweeps across the chip, an electrical signal is applied to the electrode(s) and the electrical stimulus can cause bilayer(s) to form on the electrode(s). The electrical stimulus with a voltage potential can disrupt the interface between the surface of the electrode and the lipid material around the electrodes to cause the abrupt quick formation of bilayers.

In some embodiments, the liquid lipid solution may further contain pore proteins, such as *Mycobacterium smegmatis* porin A (MspA) or alpha-hemolysin. The solution containing lipid molecules and pore proteins are dried. The surface of the chip is prepared with silane molecules to make the surface hydrophobic. Lipid molecules and pore proteins in are deposited in a powder form or in a sticky state. The user may activate the chip by applying a buffer solution to the chip. The lipid molecules and the pore proteins are hydrated. A lipid layer with nanopore inserted may be formed on top of each electrode surface. The lipid layer may form spontaneously.

In some cases, after the buffer liquid is applied into the chip, a bubble is pumped in. There may be more buffer solution behind the bubble than in front of the bubble. The bubble can sweep across the chip and smooth and thin out the newly hydrated pre-deposited lipid and pore mix and cause the lipid and/or pore molecules to sweep across the surface. After the bubble flows through, a lipid bilayer may be formed on top of each electrode surface in the manner described above or elsewhere herein, and pore proteins can be inserted in the bilayer to form nanopores.

As an alternative, or in addition to, after the bubble is applied and sweeps across the chip, an electrical signal can be applied to the electrode and the electrical stimulus may cause a bilayer to form on the electrode and nanopore to be inserted in the bilayer. The electrical stimulus with a voltage potential may disrupt the surface of the electrode and affects the lipid material around the electrodes to cause the abrupt quick formation of bilayers and nanopores in the bilayers.

In another embodiment, the semiconductor chip is solely silanized and does not have any pre-applied molecules, such as lipid molecules or pore proteins, functionalizing the surface of the chip. The surface of the chip is initially flushed using salt water, i.e., primed. Then, an aliquot of lipid in an organic solvent such as, for example, decane is inserted onto the chip. A bubble is followed to smear the lipid material and distribute and thin out the lipid material on the surface of the chip. Lipid bilayers are created over multiple electrodes via contact and distribution of the bubble. The lipid bilayers may form spontaneously.

In another related embodiment, the lipid bilayers may not be spontaneously created after the bubble. A subsequent electrical stimulation and/or other stimuli is applied to the electrodes. It is believed that the electrical pulses and/or other stimuli assists in creating a single bilayer by destroying multilayers and encouraging single bilayers to form over the electrode. The electrical pulse causes the bilayers to be formed or destroyed on the electrodes.

In yet another related embodiment, KCL is flowed across the chip and the chip is wetted, i.e., primed. Then a small amount of lipid solution is applied to the chip and flowed across the chip followed immediately by a bubble that thins and distributes the lipid across the chip. Next salt water is flowed across the chip. Following this a pore protein solution is inserted into the chip. Another bubble is followed to smear and thin the pore protein mixture on the surface of the chip so that pores are inserted over the multiple independent electrodes in an array via a form of contact or pressure from the bubble.

In still another related embodiment, after the pore protein solution and the second bubble are inserted, a subsequent electrical stimulation is applied at the electrodes to create nanopores in the lipid bilayers over the multiple electrodes in an array.

In another embodiment, an aliquot of lipid in an organic solvent such as, for example, decane gets inserted into the chip filled or covered with an ionic solution (such as salt water). A subsequent electrical stimulation is applied to the electrodes. The electrical pulse causes the bilayers to be formed on the electrodes. In this embodiment, there is no bubble inserted to facilitate bilayer formation. The lipid is well distributed around the electrodes over the surface of the chip. A voltage applied on the electrodes causes the disruption the lipid material at the edge of the electrodes and induces formation of a lipid bilayer.

The semiconductor nanopore sensor chip may contain one or more channels through which a liquid, solution and reagents can flow. In some embodiments, each channel has two rails, one on each side of the channel. The electrodes may be on the bottom surface of the channel. The electrodes may further be on the sidewall surface of the channel (on the rails). The density of electrodes for each channel may be increased by creating electrodes on the bottom and sidewall surfaces.

One or more flow cells may be utilized on the semiconductor chip. Each flow cell may be used to insert solutions and bubbles for one of the channels on the chip. A flow cell is a path that liquids, bubbles and reagents can pass through. The channels on the chip acting as entire or portions of a flow cell may be independent so that the chip can process multiple different samples independently and simultaneously.

In some embodiments, there is no channel or flow cell on the chip. The chip is pre-applied with liquid lipid solution, or liquid lipid-pore mixture solution. The solution can be dried to a powder form or a sticky state. A liquid buffer solution is applied to the chip to activate the lipid or lipid-pore mixture. An electrical signal is applied to the electrode and the electrical stimulus may cause bilayer to form on the electrode. The electrical stimulus with a voltage potential may disrupt the surface of the electrode and affects the lipid material around the electrodes to cause the abrupt quick formation of bilayers. Furthermore, if there is activated pore protein present, the electrical stimulus may further facilitate the insertion of pore molecules into the lipid bilayers.

In some embodiments, the pressure of the liquid or bubble may be varied to improve the bilayer or nanopore creation. In some embodiments, the temperature of the chip and the liquid may be varied to improve the bilayer or pore creation. For example, slightly cooler than room temperature may be applied when the bilayer is formed; slightly warmer than room temperature may be applied when the nanopore is inserted into the lipid bilayer.

A chip may have one of the four sides of the sealed chip left open and accessible. The opposite side may also have a single hole to which a tube can contact and connect. If the chip is positioned or otherwise disposed so that it is vertical with the hole and tube at the bottom and the open end of the chip at the top, buffer liquid and reagents can be added through the top and bubbles can then be released, at a controlled pace, from the bottom and travel up the sealed cavity and flow across the chip. This system may not have trains of bubbles separating liquid fractions roll across the chip. It smoothes out any substances that are added through the open top of the packaged chip and runs down the surface of the chip inside. Conversely, it is possible to insert liquids and reagents through the single tube at the bottom of the apparatus and this may be advantageous when automated time series additions of reagents may be required.

In some situations, sensor chips can be coupled to, or placed in, an apparatus that can automate the application of any combination of liquids, reagents, bubbles, electrical stimulus pulses, pressure or pressure pulses, temperature or temperature pulses, sonication pulses, and or sound pulses to the sensor chip or liquid, reagent or bubble in the sensor chip, to cause the automated creation of bilayers, creation of pores, maintenance of bilayers and pores including their re-creation, capture and reading of the biological molecules applied to the nanopore sensor chip, and to provide real-time and/or end-point details of the status of all sensors and all characteristics of the instrument' performance. The apparatus can allow any level of operator manual intervention or to allow creation of custom tests. The apparatus can apply different signals and/or reagents or act upon the sample or chip in response to the result of a prior test signal or reagent addition allowing the apparatus to operate fully or substantially automatically. Such a system can allow operator-free running of time-course experiments or allow the refreshing of the nanopore system to re-functionalize the surface of the sensor chip to continue testing.

The application of a stimulus to induce creation of bilayers or creation of pores can also include the application of any combination of buffers (pH range of about 5.0 to about 8.5), ionic solutions (e.g., NaCl, KCl; about 75 mM to about 1 M), bubbles, chemicals (e.g., hexane, decane, tridecane, etc.), physical movement, electrical stimulus or electrical stimulus pulses, pressure or pressure pulses, temperature or temperature pulses, sonication pulses, and or sound pulses to the sensor chip to stimulate the desired or otherwise predetermined bilayer/pore creation event(s).

A semiconductor chip may not contain a cover and the user may apply any and all buffers, reagents, and bubbles manually through the use of a pipette or other instrument. This manual application of these techniques can be coupled with any applied stimulus outlined herein to induce the desired bilayer and/or pore formation.

Flow cell or simple bubble systems of the present disclosure can also greatly help the insertion of pores by applying the pore protein solution evenly around the sensor chip surface and causing spontaneous pore insertion, or setting up the surface so that a stimulus of any combination of buffers (pH range of about 5.0 to about 8.5), ionic solutions (e.g., NaCl, KCl; about 75 mM to about 1 M), bubbles, chemicals (e.g., hexane, decane, tridecane, etc.), physical movement, electrical stimulus or electrical stimulus pulses, pressure or pressure pulses, temperature or temperature pulses, sonication pulses, and or sound pulses to the sensor chip can encourage the quick insertion of pores into the bilayers. A flow cell or simple bubble system can also help hydrate a dried lipid-pore-protein mix that may form both spontaneous bilayers and pores after smoothing or mixing in an appropriate buffer with or without bubbles.

Figure 23:
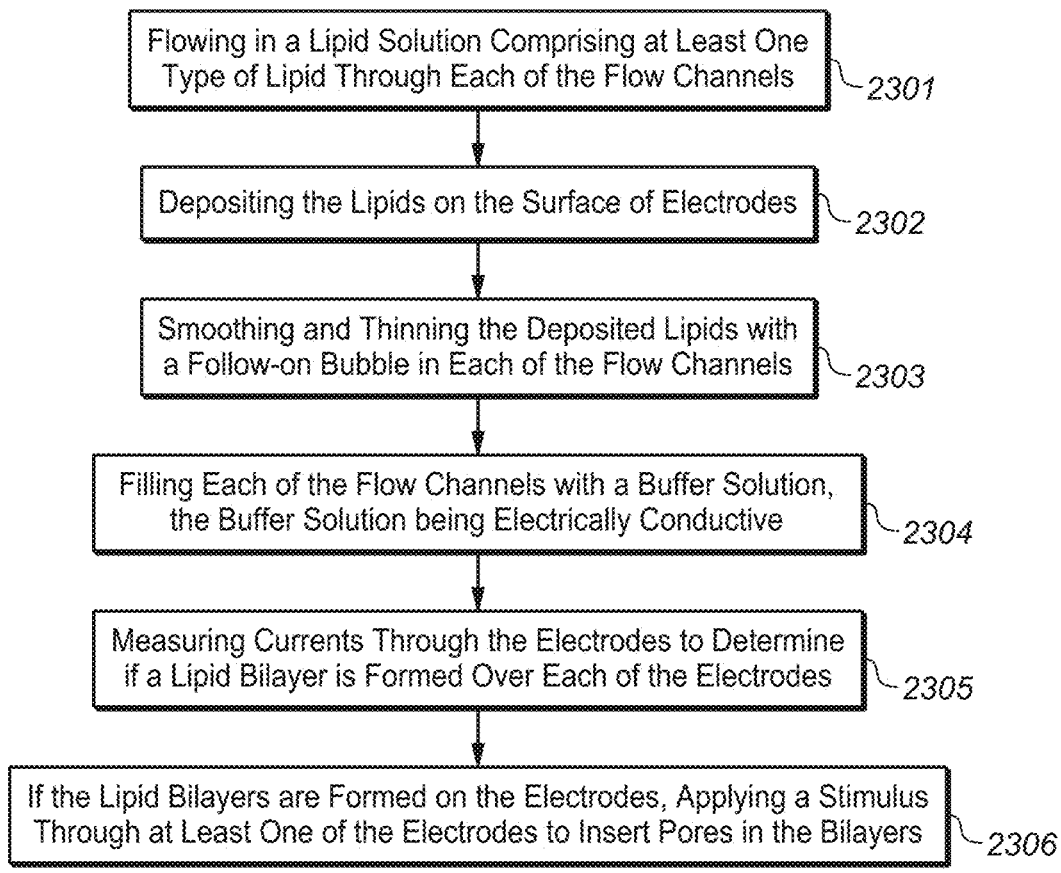
FIG. 23 shows an example of a method for forming a lipid layer over the electrodes on one or more flow channels of the primed sensor chip.

FIG. 23 illustrates a sample method for forming a lipid layer over the electrodes on one or more flow channels of a primed sensor chip. The sensor chip may be a planar chip that comprises multiple electrodes embedded in, and/or essentially planar to, a non-conductive or semiconductor surface on which is located on the surface of flow channels. The method comprises, in a first operation 2301, flowing in a lipid solution comprising at least one type of lipid through each of the flow channels. Next, in a second operation 2302, the lipids are deposited on the surface of and/or adjacent to electrodes. In a third operation 2303, the deposited lipids are smoothed and thinned with a follow-on bubble in each of the flow channels. Next, in a fourth operation 2304, each of the flow channels is once again filled with a buffer solution. The buffer solution can be electrically conductive. In a fifth operation 2305, currents are measured through the electrodes to determine if a lipid bilayer has been property formed over each the electrodes. Next, in a sixth, optional, operation 2306, if the lipid bilayers have not been properly formed on any, all or substantially all of the electrodes, a stimulus (e.g., electrical stimulus) is applied to induce the lipids on the surfaces to form lipid bilayers over the electrodes. In some instances, however, the voltage is not applied to create bilayers.

In some embodiments, the lipid solution comprises at least two types of lipids. The lipid solution may further comprise at least one type of pore proteins. The pore proteins may comprise *Mycobacterium smegmatis* porin A (MspA) or alpha-hemolysin. A non-lipid solution containing pore proteins can be directed over the deposited lipids in each of the flow channels. The pore proteins and deposited lipids can then be thinned with a bubble in each of the flow channels. Next, a pore protein solution, an additional air (or gas) bubble and an additional liquid solution can be directed through the flow channel. The pore protein solution and the liquid solution can be separated by the air bubble. An electrical stimulus can then be applied through at least some of the electrodes to facilitate an insertion of the pore protein in the lipid bilayer. The operations of flowing solutions and bubbles may be repeated in any order and combination to achieve the lipid bilayer formation and nanopore insertion in the bilayer. In some examples, the lipid are diphytanoyl-phosphatidylcholine (DPhPC), palmitoyl-oleoyl-phosphatidyl-choline (POPC), dioleoyl-phosphatidyl-methylester (DOPME), Lysophosphatidylcholine (LPC), 1,2-diphytanoyl-sn-glycero-3phosphocholine, 1,2-Di-O-Phytanyl-sn-Glycero-3-phosphocholine (DoPhPC), dipalmitoyl-phosphatidylcholine (DPPC), phosphatidylcholine, phosphatidylethanolamine, phosphatidylserine, phosphatidic acid, phosphatidylinositol, phosphatidylglycerol, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy(polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-1000]; 1,2-dipalmitoyl-sn-glycero-3-phosphoethanolamine-N-[methoxy(polyethylene glycol)-2000]; 1,2-dioleoyl-sn-glycero-3-phosphoethanolamine-N-lactosyl; GM1 Ganglioside, or sphingomyelin. The liquid lipid solution may further contain an organic solvent, such as decane.

In some embodiment, the buffer solution may contain ionic solution, such as sodium chloride or potassium chloride solution. The buffer solution may further contain Ferrous Cyanide or Ascorbic Acid, sodium glutamate, potassium glutamate, tetramethylammonium chloride, tetraethylammonium chloride, ammonium chloride, etc. Also may contain trehalose, sucrose, or any other sugar. The buffer may also contain divalents such as magnesium chloride, calcium chloride, strontium chloride, manganese chloride, etc. In some embodiments, the pressure of the bubbles and/or fluid is adjusted substantially at or slightly above or below the atmospheric pressure to improve the bilayer formation or nanopore insertion.

FIG. 24 illustrates a sample semiconductor sensor chip, in accordance with an embodiment of the present disclosure. The sensor chip 2400 comprises multiple flow channels 2410. Each flow channel has multiple electrodes 2440 embedded in, and planar or substantially planer to, a non-conductive or semiconductor surface on which is located on the surface of the flow channels 2410. The surface of the flow channel other than the electrodes is hydrophobic. The surfaces of the flow channel other than the electrodes can be hydrophobic, hydrophilic, or any combination thereof. Different walls may be treated for different characteristics. The flow channels 2410 are separated by guide rails 2420 along the flow channels. The channel width may be wide enough to accommodate two or more rows electrodes. The electrodes may be fabricated on the bottom surface of the flow channels, as well as the side walls of the guide rails, as shown in FIG. 24. In some embodiments, the top side of the flow channels is sealed.

In another aspect, a method for forming a lipid bilayer over the electrodes on one or more flow channels of a primed sensor chip, i.e., a chip that has had the buffer solution flowed over the chip, comprises: (a) flowing in a lipid solution comprising at least one type of lipids through each of the flow channels; (b) depositing the lipids on the surface of the chip; (c) smoothing and thinning the deposited lipids with a follow-on or additional bubble in each of the flow channels; (d) further flowing buffer solution through each of the flow channels, the buffer solution being electrically conductive; (e) measuring currents through the electrodes to determine if a lipid bilayer is formed over each the electrodes; and (f) if the lipid bilayers are not formed on any of the electrodes, optionally, applying a stimulus to at least one of the electrodes to induce the lipids on the surfaces to form lipid bilayers over the electrodes. The stimulus can comprise at least one of an electrical pulse, sonication pulse, pressure pulse, and sound pulse, or any combination of buffers (pH range of about 5.0 to about 8.5), ionic solutions (e.g., NaCl, KCl; about 75 mM to about 1 M), bubbles, chemicals (e.g., hexane, decane, tridecane, etc.), physical movement, electrical stimulus or electrical stimulus pulses, pressure or pressure pulses, temperature or temperature pulses, sonication pulses, and or sound pulses to the sensor chip.

In some embodiments, the lipid solution comprises at least two types of lipids. In some embodiments, the lipid solution further comprises at least one type of pore protein.

In some embodiments, after (c): a non-lipid solution containing pore proteins is directed over the deposited lipids in each of the flow channels. The pore proteins and deposited lipids can then be thinned with a second bubble in each of the flow channels. The operations above may be repeated at least 1 time, 2 times, 3 times, 4 times, 5 times, or more times in any order or combination.

In some cases, a pore protein solution, an additional air bubble and an additional liquid solution can be directed through the flow channel. The pore protein solution and the liquid solution can be separated by the air bubble. Next, a stimulus, for example, any combination of buffers (pH range of about 5.0 to about 8.5), ionic solutions (e.g., NaCl, KCl; about 75 mM to about 1 M), bubbles, chemicals (e.g., hexane, decane, tridecane, etc.), physical movement, electrical stimulus or electrical stimulus pulses, pressure or pressure pulses, temperature or temperature pulses, sonication pulses, and or sound pulses to the sensor chip, can be applied through at least some, all or substantially all of the electrodes to facilitate an insertion of the pore protein in the lipid bilayer.

In some embodiments, the lipid is diphytanoylphosphatidylcholine (DPhPC), palmitoyl-oleoyl-phosphatidyl-choline (POPC), 1,2-diphytanoyl-sn-glycero-3phosphocholine, 1,2-Di-O-Phytanyl-sn-Glycero-3-phosphocholine (DoPhPC), dioleoyl-phosphatidyl-methylester (DOPME), dipalmitoylphosphatidylcholine (DPPC), Lysophosphatidylcholine (LPC), phosphatidylcholine, phosphatidylethanolamine, phosphatidylserine, phosphatidic acid, phosphatidylinositol, phosphatidylglycerol, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy(polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-1000]; 1,2-dipalmitoyl-sn-glycero-3-phosphoethanolamine-N-[methoxy (polyethylene glycol)-2000]; 1,2-dioleoyl-sn-glycero-3-phosphoethanolamine-N-lactosyl; GM1 Ganglioside, or sphingomyelin.

In some cases, at least some of the liquid lipid solutions contain an organic solvent (e.g., decane). The pore proteins, in some examples, can comprise *Mycobacterium smegmatis* porin A (MspA) or alpha-hemolysin. In some cases, the buffer solution contains an ionic solution containing one or more ions (e.g., sodium chloride or potassium chloride). In some instances, at least some of the buffer solution contains ferrous cyanide or ascorbic acid. In some instances, the buffer solution may also contain sodium glutamate, potassium glutamate, tetramethylammonium chloride, tetraethylammonium chloride, ammonium chloride, ferrocyanide, ferricyanide, potassium acetate, etc. In some instances, the buffer solution may also contain trehalose, sucrose, or any other sugar. In some instances, the buffer solution may also contain divalents such as magnesium chloride, calcium chloride, strontium chloride, manganese chloride, etc.

In some embodiments, the pressure of the bubbles and/or fluid is substantially at or slightly above atmospheric pressure. The bubbles can have a pressure that is greater than atmospheric, such as at a pressure that is a magnitude of 101 kPa to 1013 kPa.

The surface of the metal electrodes is hydrophilic. In the instance when the electrodes may not be metal; such as conductive silicon, a potential voltage, or varying potential voltage, can be applied to the electrodes during the silanization process to discourage silane from adhering and reacting to the non-metal electrodes. Voltages of ±10 mV up to ±2V and differing concentrations of low ionic buffer with the silane mix can be used. It is also possible to remove any reacted or residual silane from metal or non-metal electrodes by cycling voltages at the electrodes and "burning off" the silane after deposition. For non-metal electrodes, after burning off a hydrophobic silane step a hydrophilic silane step may be added and only the space over the electrode will be open to react to the silane. The result is an electrode surface that is not hydrophobic and not lipohillic and should be hydrophilic.

In some instances, the surface of the flow channel other than the electrodes is hydrophobic. In some embodiments, the surfaces of the flow channel (other than the electrodes) can be hydrophobic, hydrophilic, or any combination thereof. Different surfaces (walls or channel floor) may be treated for different characteristics.

In some embodiments, before (a), the surface of the flow channel other than the electrodes can be rendered hydrophobic by silanizing, chemically treating, or using or designing specific materials, the surface of the flow channel other than the electrodes; a plurality of flow channels can be formed on a surface of the chip; the electrodes can be fabricated on a surface of each of the flow channels; the flow channels can be separated by by building guide rails along the flow channels; the electrodes can be fabricated on a side surface of each of the guide rails; and/or the top side of each of the flow channels can be sealed.

In some situations, a chip having a bilayer can be created by flowing an ionic solution across the chip. The flow can be a "train" of interspersed lipid solution and ionic solution aliquots (e.g., alternating lipid solution and ionic solution). The flow can go through supply tubing and across the chip. In some examples, a train can have at least or approximately 0.1 uL, 1 uL, 2 uL, 3 uL, 4 uL, or 5 uL of lipid and then at least or approximately 0.1 uL, 1 uL, 2 uL, 3 uL, 4 uL, or 5 uL of ionic solution, and can be repeated 1, 2, 3, 4, 5, 6, 7, 8, 9, 10, or more times. The train of solutions can be pumped back and forth across the surface of the biochip approximately 2, 3, 4, 5, 6, 7, 8, 9, 10, or more times. The coverage and/or seal can then be electrically checked. In some embodiments, the train of lipid and/or ionic solution(s) may be between about 0.1 uL to about 1000 uL.

In some cases, the train of solutions is followed by an assembly operation. The assembly operation can involve flowing a bubble across the chip. In some instances, electrical methods can be used to check the coverage of cells (including electrodes) and/or leakage or seal resistance at each electrode.

In some cases, the assembly operation is repeated until at least some or all of the following test results are attained: (1) at least about 100, 150, 160, 170, 180, 190, 200, 210, 220, 230, 240, 250, or more electrodes are covered; (2) At least about 100, 110, 120, 130, 140, 150, 160, 170, 180, 190, or 200 membranes (e.g., lipid layers) are popped at an applied voltage of less than −1V; (3) of the lipid layers that popped in (2), at least 40, 50, 60, 70, 80, 90, 100, or more have popped between about −300 mV to −700 mV; (4) the number of electrodes with a seal resistance less than about 50 Giga-ohms is less than 30, 20, 15, or 10; and (5) if the number of cells which show any recorded leakage current exceeds 50 then the median of the seal resistance is greater than 150 Giga-ohms. In some cases, the assembly operation is repeated until at least some or all of the following test results are attained: (1) at least about 10%, 20%, 30%, 40%, 50%, 60%, 70%, 80%, 90%, 95%, or more, e.g., 100%, electrodes are covered; (2) At least about 10%, 20%, 30%, 40%, 50%, 60%, 70%, 80%, 90%, 95%, or more, e.g., 100%, membranes (e.g., lipid layers) are popped at an applied voltage of less than ±1V; (3) of the lipid layers that popped in (2), at least 10%, 20%, 30%, 40%, 50%, 60%, 70%, 80%, 90%, 95%, or more, e.g., 100%, have popped between about ±300 mV to ±700 mV; and (4) a minimum number of cells that have greater than 10 GOhms (e.g., at least 10%, 20%, 30%, 40%, 50%, 60%, 70%, 80%, 90%, or 100%).

If some or all of these criteria are met, then a bubble of any size between approximately 10 microliters (uL) to about 1000 uL can be flowed across the chip, followed by an amount of buffer (e.g., about 10 uL to about 10 mL) and a final test of (1), (4), and (5) can be performed. If this passes, then the program moves to pore insertion protocol. The program can be implemented with the aid of a computer system (e.g., upon execution by a processor).

In some cases, the pore insertion protocol includes applying at least or about 0.1 uL, 1 uL, 2 uL, 3 uL, 4 uL, 5 uL or up to about 1 mL of pore protein solution to the chip and applying a stimulus, e.g., electroporating, to insert the pores into the bilayer. At the end of the electroporation operation, the chip may be checked for pore yield and if the criteria are passed, sample and test reagents are applied.

The total time for bilayer creation and pore insertion can be any suitable value. In some cases, the total time is about 1 minute, about 5 minutes about 10 minutes, about 20 minutes, about 30 minutes, about 45 minutes, about 1 hour, or about 2 hours. In some cases, the total time is less than about 1 minute, less than about 5 minutes less than about 10 minutes, less than about 20 minutes, less than about 30 minutes, less than about 45 minutes, less than about 1 hour, or less than about 2 hours. In some instances, about 10%, about 20%, about 30%, about 40%, about 50%, about 60%, about 70%, about 80%, or about 90% of the total time is for bilayer formation. Any proportion of the total time can be split between bilayer formation and pore insertion. In some cases, the bilayer is formed and the nanopore is inserted simultaneously. In some instances, the total time for bilayer and pore insertion is, on average, 15 minutes for bilayer creation and 20 minutes for pore insertion for a total of 35 minutes.

Any number of wells can be covered by a membrane (e.g., lipid bilayer) with inserted pore (e.g., pore yield). In some cases, the pore yield is about 10%, about 20%, about 30%, about 40%, about 50%, about 60%, about 70%, about 80%, about 90%, and the like. In some cases, the pore yield is at least about 10%, at least about 20%, at least about 30%, at least about 40%, at least about 50%, at least about 60%, at least about 70%, at least about 80%, at least about 90%, and the like.

In some embodiments, the parameters applied to the electrode chip and to a test set-up are 1M KCl or 300 mM NaCl, pH 7.5 (pH range between about 5.0 to about 8.5), current fluidic flow rates (e.g., between about 1 uL/sec to about 1000 uL/sec), sea level atmospheric pressure, and room temperature.

Use of a Gel to Support the Membrane

In an aspect, a method for forming a biochip or sensor comprises coating a substrate with a layer suitable for adhesion of a membrane (e.g., a lipid bilayer comprising a nanopore). The substrate can be silanized with an organo-functional alkoxysilane molecule. FIG. 18 shows a biochip where a membrane can be disposed on the silanized surface.

Figure 19:
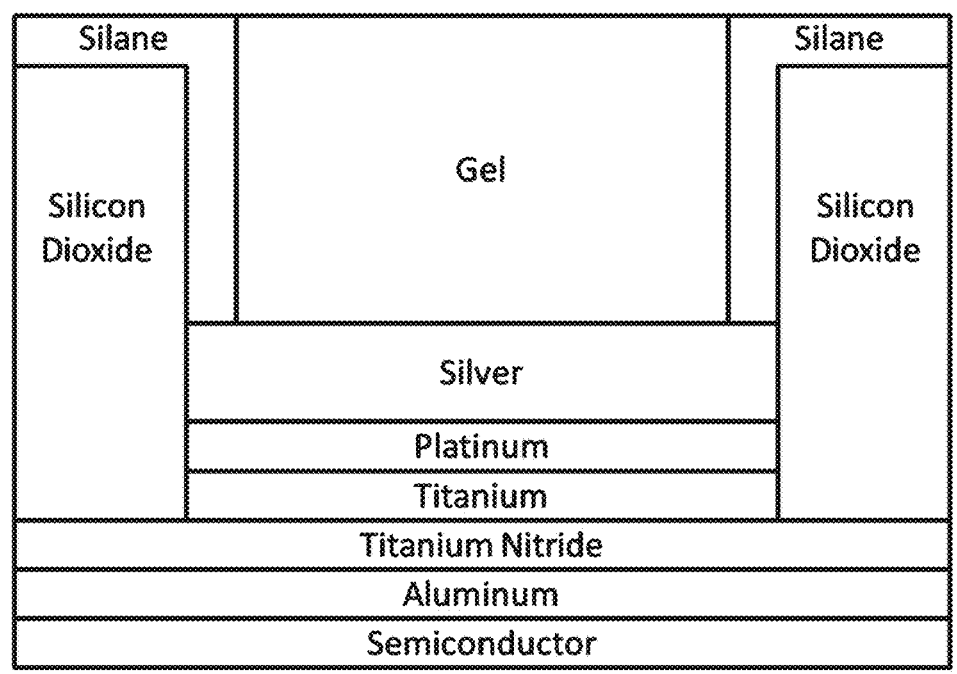
FIG. 19 shows the filling of the well with a gel.
Figure 20:
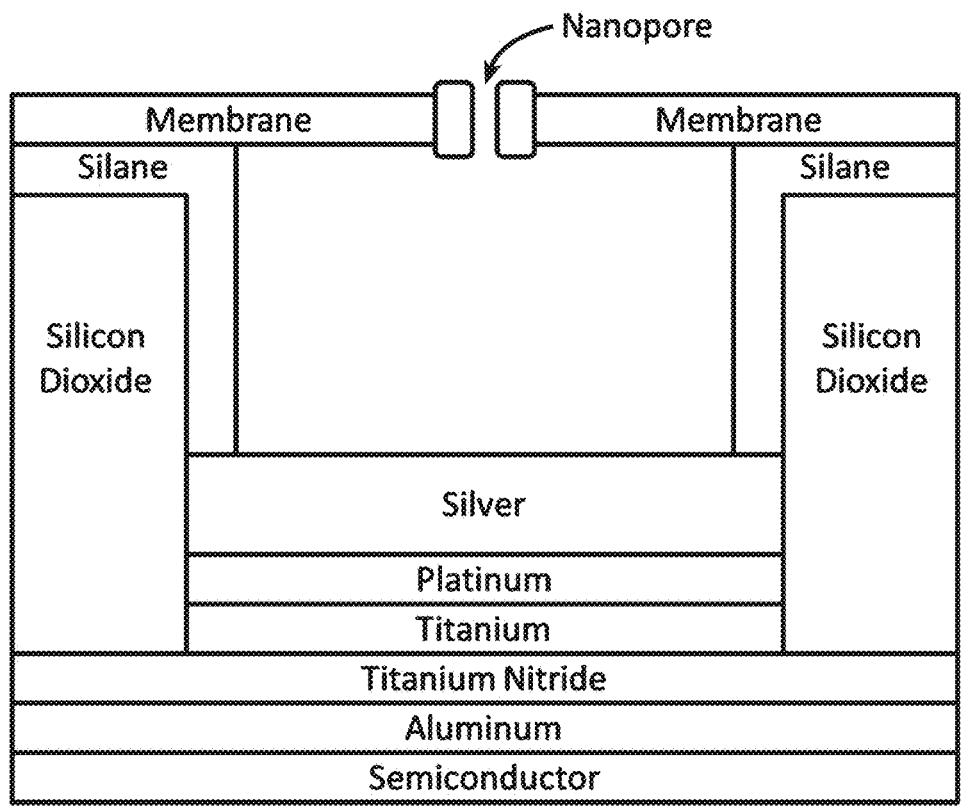
FIG. 20 shows creation of a membrane with a nanopore over the well.

In some cases, the membrane is difficult to form and/or is unstable at least in part due to the membrane being supported on the silanized silicon dioxide, but not supported over the well. It is recognized and described herein that filling the well with a gel can support the membrane over the well area, thereby making it easier to form the membrane and/or stabilizing the membrane. In some embodiments, the empty portion of a well is filled with a gel as shown in FIG. 19. The gel can provide mechanical support for a membrane disposed over the well.

In other embodiments, the membrane may be stabilized chemically through the use of buffers comprising trehalose, or other sugars.

In an aspect, a method for preparing a biochip comprises: (a) depositing a gel into well that is in proximity to an electrode and sensing circuit; and (b) forming a membrane over the well, wherein the membrane is at least partially supported by the gel.

In various embodiments, the gel is non-reactive, cross-linked, comprises a liquid electrolyte, or any combination thereof. Gels can include but are not limited to standard reagent gels such as agarose and commercially available proprietary gel matrixes. Examples are Collagen, Lamanin, Hydrogels, QGel, and HydroMax gels.

Insertion of a Nanopore

In some instances, a nanopore is inserted in the membrane (e.g., by electroporation). The nanopore can be inserted by a stimulus signal such as electrical stimulus, pressure stimulus, liquid flow stimulus, gas bubble stimulus, sonication, sound, vibration, or any combination thereof. The nanopore can be a protein nanopore such as alpha-hemolysin or *Mycobacterium smegmatis* (MspA) nanopore or a nanopore that has at least about 70% homology to either alpha-hemolysin or MspA.

In some embodiments, inserting the nanopore comprises applying a stimulus (e.g., electroporation pulse) through said electrode to facilitate the insertion of said nanopore. In some cases, this is followed by a second electrical detection pulse to detect the insertion of said nanopore in said lipid bilayer. The use of an electroporation pulse followed by detection pulse can be repeated quickly and/or many times and with sequentially varying voltage levels used for the electroporation pulse until a pore is inserted and detection is achieved. In an embodiment, the initial electroporation pulse is about 50 mV (positive or negative) one to ten times repeated with each subsequent batch of electroporation pulse(s) increasing from the previous electroporation pulse by about 1 mV to a maximum of about ±700 mV, i.e., a staircase of increasing voltage. The detection pulse is +160 mV between each electroporation pulse. Thus, for example, the process of inserting a nanopore in a lipid bilayer would be application of a 50 mV electroporation pulse and application of a detection pulse five times, application of a 51 mV electroporation pulse and application of a detection pulse five times, etc. The process is repeated until a nanopore is inserted in which case the electrode is turned off, or until the electrode/well is rejected or determined to have failed.

In some cases, an enzyme, e.g., polymerase (e.g., DNA polymerase) or other enzyme (e.g., reverse transcriptase), is attached to and/or is located in proximity to the nanopore. The polymerase/enzyme can be attached to the nanopore before or after the nanopore is incorporated into the membrane. In some instances, the nanopore and polymerase/enzyme are a fusion protein (i.e., single polypeptide chain). It is to be understood that although a polymerase is exemplified throughout that any suitable enzyme could be used.

The polymerase can be attached to the nanopore in any suitable way. In some cases, the polymerase is attached to the hemolysin protein monomer and then the full nanopore heptamer is assembled (e.g., in a ratio of one monomer with an attached polymerase to 6 hemolysin monomers without an attached polymerase). The nanopore heptamer can then be inserted into the membrane.

Another method for attaching a polymerase to a nanopore involves attaching a linker molecule to a hemolysin monomer or mutating a hemolysin monomer to have an attachment site and then assembling the full nanopore heptamer (e.g., at a ratio of one monomer with linker and/or attachment site to 6 hemolysin monomers with no linker and/or attachment site). It is understood that the combination of monomer with a linker and/or attachment site ($H^+$) to hemolysin monomers with no linker and/or attachment site ($H^-$) may be done to achieve the heptameric hemolysin nanopore with any ratio of the subunits, e.g., $(H^+)_2(H^-)_5$, $(H^+)_3(H^-)_4$, $(H^+)_4(H^-)_3$, etc. A polymerase can then be attached to the attachment site or attachment linker (e.g., in bulk, before inserting into the membrane). The polymerase can also be attached to the attachment site or attachment linker after the (e.g., heptamer) nanopore is formed in the membrane. In some cases, a plurality of nanopore-polymerase pairs are inserted into a plurality of membranes (e.g., disposed over the wells and/or electrodes) of the biochip. In some instances, the attachment of the polymerase to the nanopore complex occurs on the biochip above each electrode.

The polymerase can be attached to the nanopore with any suitable chemistry (e.g., covalent bond and/or linker). In some cases, the polymerase is attached to the nanopore with molecular staples. In some instances, molecular staples comprise three amino acid sequences (denoted linkers A, B and C). Linker A can extend from a hemolysin monomer, Linker B can extend from the polymerase, and Linker C then can bind Linkers A and B (e.g., by wrapping around both Linkers A and B) and thus the polymerase to the nanopore. Linker C can also be constructed to be part of Linker A or Linker B, thus reducing the number of linker molecules. Linkers may also be biotin and streptavidin.

In some instances, the polymerase is linked to the nanopore using Solulink™ chemistry. Solulink™ can be a reaction between HyNic (6-hydrazino-nicotinic acid, an aromatic hydrazine) and 4FB (4-formylbenzoate, an aromatic aldehyde). In some instances, the polymerase is linked to the nanopore using Click chemistry (available from LifeTechnologies for example). In some cases, zinc finger mutations are introduced into the hemolysin molecule and then a molecule is used (e.g., a DNA intermediate molecule) to link the polymerase to the zinc finger sites on the hemolysin.

Methods for Detecting Bilayer Formation

After an attempt to create bilayers on the sensor described above, an electrical stimulus can be applied to determine whether a bilayer has been established or if the electrodes are simply covered with a non-bilayer layer. One way to do this is to apply a non-disruptive AC stimulus to the layer-covered electrodes and look for capacitive current responses that indicate the electrode is covered with a thin capacitive lipid bilayer (or other thin layer).

If appropriate capacitive readings are detected for the salt, voltage, and electrode diameter conditions then it can be inferred that a bilayer has been created over the electrode and the operator is ready to begin the pore insertion step.

Alternately, a distructive application of sequentially increasing voltage pulses can be applied to each electrode of the array and the voltage at which the layer over the electrode breaks is recorded. If the voltages seen across an acceptable number of electrodes correspond to anticipated bilayer-break voltages for the salt, voltage, and electrode diameter conditions, then a single bubble is flowed across the chip re-make the bilayers and the operator is ready to begin the pore insertion step.

Systems for Forming Wells and Nanopore Devices

Another aspect of the disclosure provides systems for forming nanopore devices, including wells. Such systems can be used to form membranes (e.g., lipid bilayers) adjacent to the wells or electrodes, and insert nanopores in the membranes.

The system can include a deposition system, a pumping system in fluid communication with the deposition system, and a computer system (or controller) having a computer processor (also "processor" herein) for executing machine readable code implementing a method for forming the wells. The code may implement any of the methods provided herein. The pumping system can be configured to purge or evacuate the deposition system. In some cases, the deposition system is precluded.

The deposition system can include one or more reaction spaces for forming material layers of the wells. In some situations, the deposition system is a roll-to-roll deposition system with one or more interconnected reaction chambers, which can be fluidically isolated from one another (e.g., with the aid of purging or pumping at locations in-between the chambers).

One or more deposition systems can be used to form a well. A deposition system can be configured for use with various types of deposition techniques, such as, for example, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD) and physical vapor deposition (e.g., sputter deposition, evaporative deposition). A deposition system can be configured to enable layer-by-layer formation using various semiconductor manufacturing techniques, such as photolithography.

The pumping system can include one or more vacuum pumps, such as one or more of a turbomolecular ("turbo") pump, a diffusion pump, ion pump, cryogenic ("cryo") pump, and a mechanical pump. A pump may include one or more backing pumps. For example, a turbo pump may be backed by a mechanical pump.

In some situations, an array comprising one or more wells is formed in a substrate with the aid of a deposition system. Deposition may be regulated with the aid of a controller. In some embodiments, the controller is configured to regulate one or more processing parameters, such as the substrate temperature, precursor flow rates, growth rate, carrier gas flow rate and deposition chamber pressure. The controller includes a processor configured to aid in executing machine-executable code that is configured to implement the methods provided herein. The machine-executable code is stored on a physical storage medium, such as flash memory, a hard disk, or other physical storage medium configured to store computer-executable code.

A controller can be coupled to various components of the system. For instance, the controller can be in communication with the one or more deposition systems and/or fluid flow systems (e.g., pumping systems). The controller can be in communication with the pumping system, which can enable the controller to regulate a pressure of the enclosure.

A controller can be programmed or otherwise configured to regulate one or more processing parameters, such as the substrate temperature, precursor flow rates, growth rate, carrier gas flow rate, precursor flow rate, and deposition chamber pressure. The controller, in some cases, is in communication with a valve or a plurality of valves of a deposition chamber, which aids in terminating (or regulating) the flow of a precursor in the deposition chamber. The controller includes a processor configured to aid in executing machine-executable code that is configured to implement the methods provided herein. The machine-executable code is stored on a physical storage medium, such as flash memory, a hard disk, or other physical storage medium configured to store computer-executable code. The controller can also be used to regulate membrane and/or pore formation, such as the flow of a lipid solution into a fluid flow path, the flow of one or more bubbles in the fluid flow path, and the application of one or more stimuli (e.g., electrical stimulus).

Aspects of the systems and methods provided herein can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Methods for forming lipid bilayers, inserting nanopores in lipid bilayers, and sequencing nucleic acid molecules can be found in PCT Patent Publication No. WO2011/097028, which is incorporated herein by reference in its entirety. In some cases, the membrane is formed with aid of a bubble and the nanopore is inserted in the membrane with aid of an electrical stimulus.

Described herein are uses of the biochips and/or biochips produced by the methods described herein. The biochips may be used to determine the presence of methylated nucleic acid bases in a sequence of nucleic acid bases.

The biochips described herein may be used to determine the effect of drugs or any man-made or naturally occurring molecule on the stability or performance of trans-membrane proteins or membrane bound proteins. The detector can be set up by creating an array (e.g., greater than 2) of individually addressable electrodes over which artificial or natural cell membranes, or any insulating layer, are made as described herein. Into these membranes, layers, or insulating layers, any number of pre-selected or unknown trans-membrane proteins may be inserted using the methods described herein. Any trans-membrane protein can be inserted into the lipid bilayer (or any insulating layer) and the effects of chemicals, drugs, and any biological or man-made molecule on the stability or performance of these trans-membrane proteins can be electrically sensed and detected, for example by detecting the disruption of the membrane after application of a specific drug. Any trans-membrane protein whose presence can be detected ionically or electrically provides even more information in the above assay as changes in the molecules response to electrical stimulus can be correlated with the application of specific drugs or changes in the environment impressed on the bilayer/pore.

The biochips described herein may be used to determine the effect of drugs or any man-made or natural molecules on the stability or performance of different membranes placed over different portions of the array sensor. By using the channels defined in the drawings of this application different lipid bilayer materials or insulating layers may be directed to different areas of the array chip, and a plurality of different lipid membranes or insulating layers can be presented to a test solution, each membrane/layer type present at a known location. The ability of drugs to influence membrane/layer types or any man-made or naturally occurring molecule to effect the different membranes can be detected.

The biochips described herein may be used to detect the presence of, capture, sort, and bin specific proteins or specific biomolecules in an unknown solution.

The biochips and methods of making and using biochips described herein can use an electrolyte solution. In some cases, the ions in the electrolyte solution flow through the nanopore and are detected by the electrode. In cases where the electrode is a sacrificial electrode (i.e., depleted during detection, e.g., silver) the electrode can last relatively longer when the electrolyte comprises some salts rather than others. In some embodiments, the electrolyte does not comprise potassium ion (e.g., because potassium ion results in a relatively shorter electrode life). In some embodiments, the electrolyte comprises lithium chloride, tetramethylammonium chloride, triethylammonium chloride, ammonium chloride, sodium chloride, potassium glutamate, sodium glutamate, or any combination thereof (e.g., because the listed salts result in a relatively shorter electrode life).

Biochips of the disclosure can perform sensing measurements with the aid of resistive, inductive or capacitive sensing. In some cases, a biochip comprises an electrode that can sense a capacitance of a membrane adjacent to the electrode upon interaction of the membrane or a nanopore in the membrane with a species adjacent or in proximity to the membrane or the nanopore. Such measurements can be made with the aid of an applied alternating current (AC) waveform or a direct current (DC) waveform.

EXAMPLES

The examples below are illustrative of various embodiments of the present disclosure and non-limiting.

Example 1. Forming Bilayers and Inserting Pores

Forming bilayers and inserting pores on the flow cell using a manual syringe setup and an automated syringe pump setup results in high bilayer and single hemolysin pore yield. Bilayers are formed on both setups via flowing 1M or 0.3M KCl solution and air bubbles across a lipid covered chip surface and applying electrical stimuli. Two hemolysin application methods result in high single pore yield. One method involves the following operations: (1) premix hemolysin with lipid in decane, (2) flow the hemolysin-lipid mixture over the chip surface and incubate for a few minutes, (3) form bilayers, and (4) apply an electrical stimulus to electroporate pores into bilayers. The second method involves the following operations: (1) Flow KCl over the surface of the chip, (2) flow lipid in decane over the chip surface, (3) form bilayers, (4) flow hemolysin across the chip surface, or hemolysin and reaction mix across chip surface (5) apply an electrical stimulus to electroporate pores into bilayers, and (6) flow KCl across chip surface to remove free hemolysin The method can be followed by reagent mixing or simply leaving the hemolysin and reagent to mix on the chip before beginning to take readings. During the electroporation operation in both application methods, the chip can be heated up to make bilayers more fluidic for easier hemolysin insertion. The temperature is reduced to room temp or lower either during or after the electroporation operation to increase longevity of pore life.

Example 2. Flow Cell Configuration

Figure 25B:
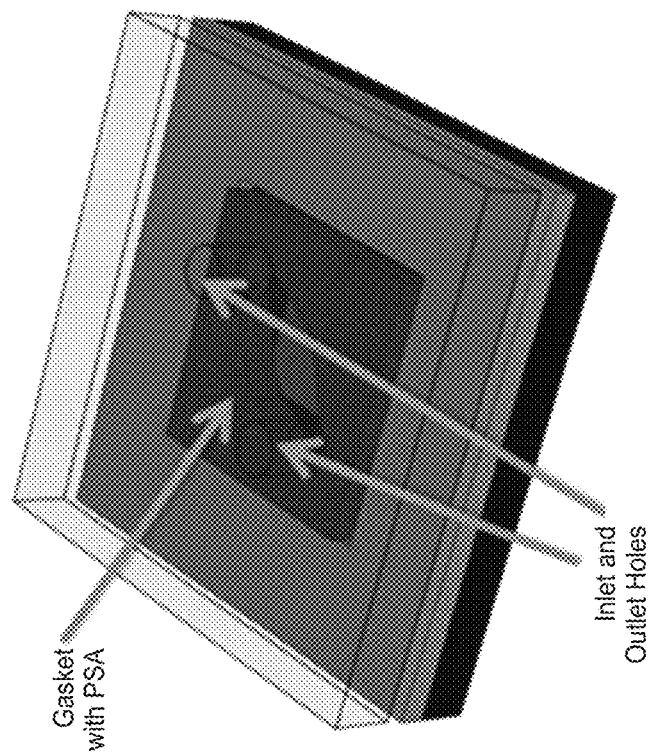
FIG. 25B shows the flowcell of FIG. 25A wherein the rigid plastic top is depicted transparently.
Figure 25A:
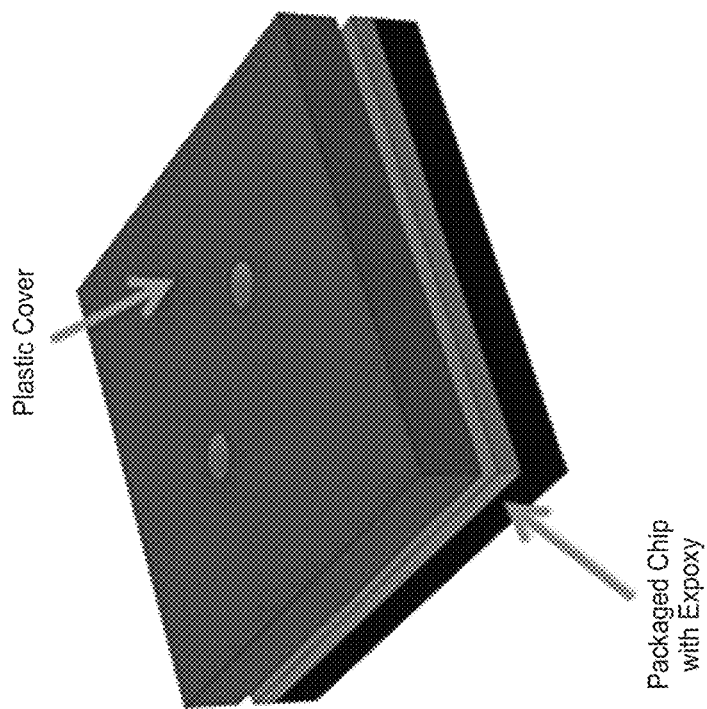
FIG. 25A shows an example flowcell configuration wherein a gasket is placed directly on top of a semiconductor chip having a rigid plastic top position on top of the gasket.
Figures 25C, 26:
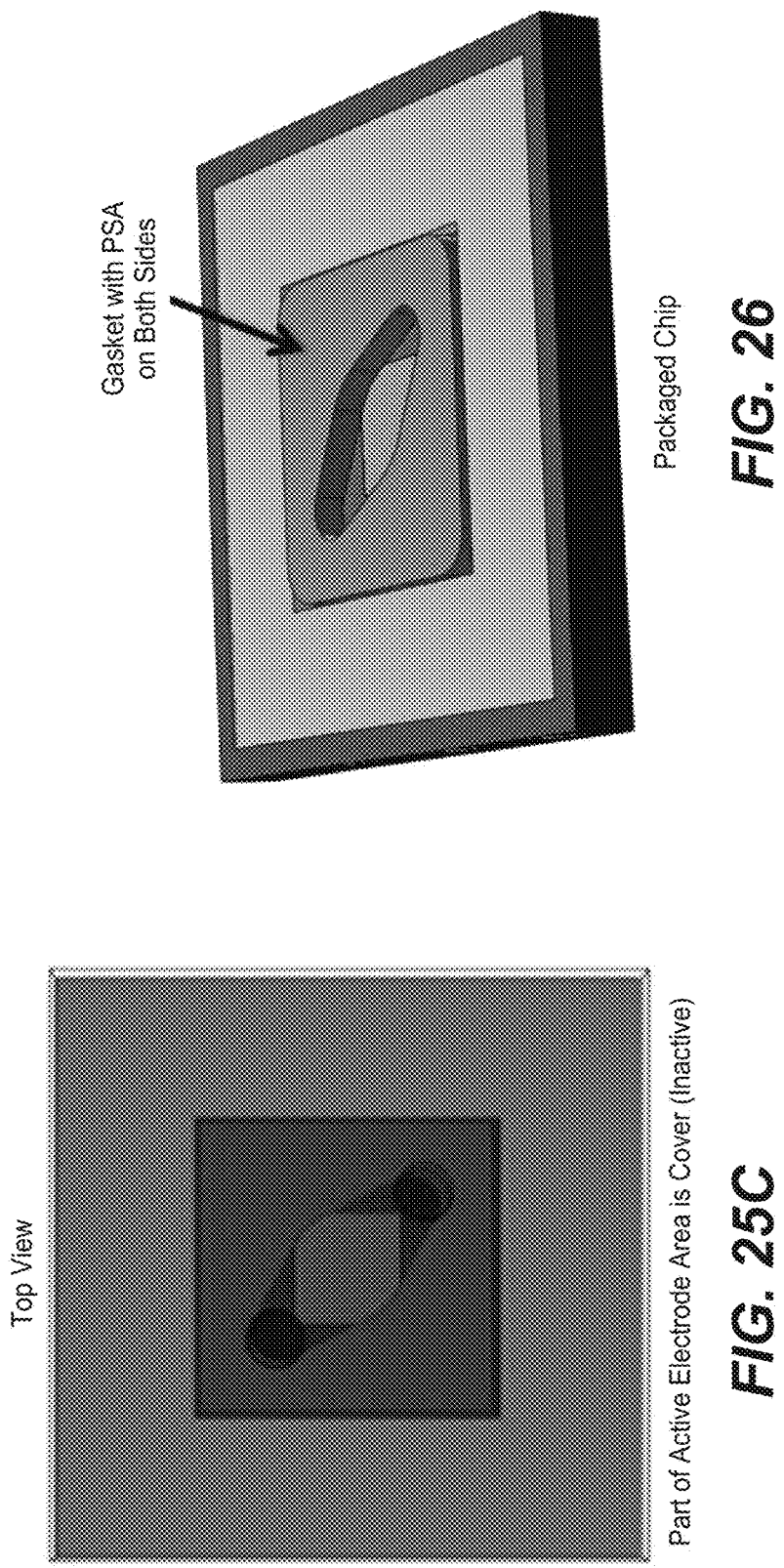
FIG. 25C shows a top view of the flowcell of FIG. 25A wherein the rigid plastic top is depicted transparently.
FIG. 26 shows an example of a packaged chip.

With reference to FIGS. 25A-C and FIG. 26, the flow cell is assembled on the chip package by directly placing a gasket on top of the semiconductor chip FIG. 25A. The gasket thickness varies from 50 um to 500 um. The gasket can be composed of plastic with pressure sensitive adhesives on one or both sides, silicone membrane, or flexible elastomer, such as EPDM. The gasket can be made into any shape. A rigid plastic top (e.g., made from PMMA) is positioned on top of the gasket (e.g., made from PSA laminated PMMA) and can be sealed to the gasket through the pressure sensitive adhesive or by a locking mechanism that applies a compression force to the gasket. The top has single or multiple inlet and outlet ports FIGS. 25B and 25C used to flow reagents and air through the flow cell.

In some instances the overall gasket size is 4 mm by 4 mm square. In some cases, the flowcell volume is about 1.5 ul for the 500 um thick gasket configuration. About 15 to 20 electrodes are covered under the gasket in some embodiments.

Example 3. Bilayer Forming Protocol

1. Wet the chip surface by flowing over 300 mM KCl over chip/through channels.
2. Flow through 20 uL 7.5 mg/ml DPhPC in decane followed by 120 uL 300 mM KCl, 20 mM HEPES, pH 7.5 ("KCl").
3. Apply a series of negative electric pulses ranging from ±250 mV to ±1V with a 30 pA deactivation.
4. Wash chip with 2× (20 uL KCl, 20 uL bubble) then 120 uL KCl.
5. Repeat Step 3.
6. Repeat operations 4 and 5 until at least 30% of cells deactivate between magnitude of 300 mV and 700 mV pulses (e.g., about 4 to 8 times).
7. Recover cells with 2× (20 uL KCl, 20 uL bubble) and 120 uL KCl.

Step 6 is a destructive test to test for single lipid bilayers, versus multilaminar, multistack or non-bilayer configurations. Optimal performance is achieved with single bilayer configurations.

The bubbles used in steps 4 and 6, above, ranged from about 2 uL to about 300 uL. The flow rate (of liquids and bubbles) ranged from about 1 uL/sec to about 250 uL/sec, with a preferred flow rate of about 10 uL/sec.

This was performed manually. An automated method is described in Example 6, below.

Example 4. Pore Insertion Protocol

Method 1: mix hemolysin with lipid at start of experiment
1. After forming bilayers, set hand warmers on top of flow cell.
2. Electroporate pores into bilayers with a series of negative electric pulses ranging from −50 mV to −600V with a 10 pA deactivation.

The plate is then washed with 300 mM KCl to remove excess hemolysin.

Method 2: flow hemolysin over bilayers followed with a wash-first electroporation:
1. After forming bilayers, flow 20 ul of 100 ug/mlhemolysin in 0.3M KCl in 20 mM HEPES, pH 7.5 ("KCl"), and 5% glycerol through flow cell.
2. Wash with 20 ul bubble and 80 uL 0.3M KCl, pH 7.5. Wash away excess hemolysin with 300 mM KCl, pH 7.5.
3. Electroporate pores into bilayers with temperature set warmer than room temperature.

Method 3: Bilayer Formation with hemolysin electroporation
1. Same as Method 2 except no wash step (Step 2).

Example 5. Bilayer Formation and Pop Automated with Pump

Figure 27:
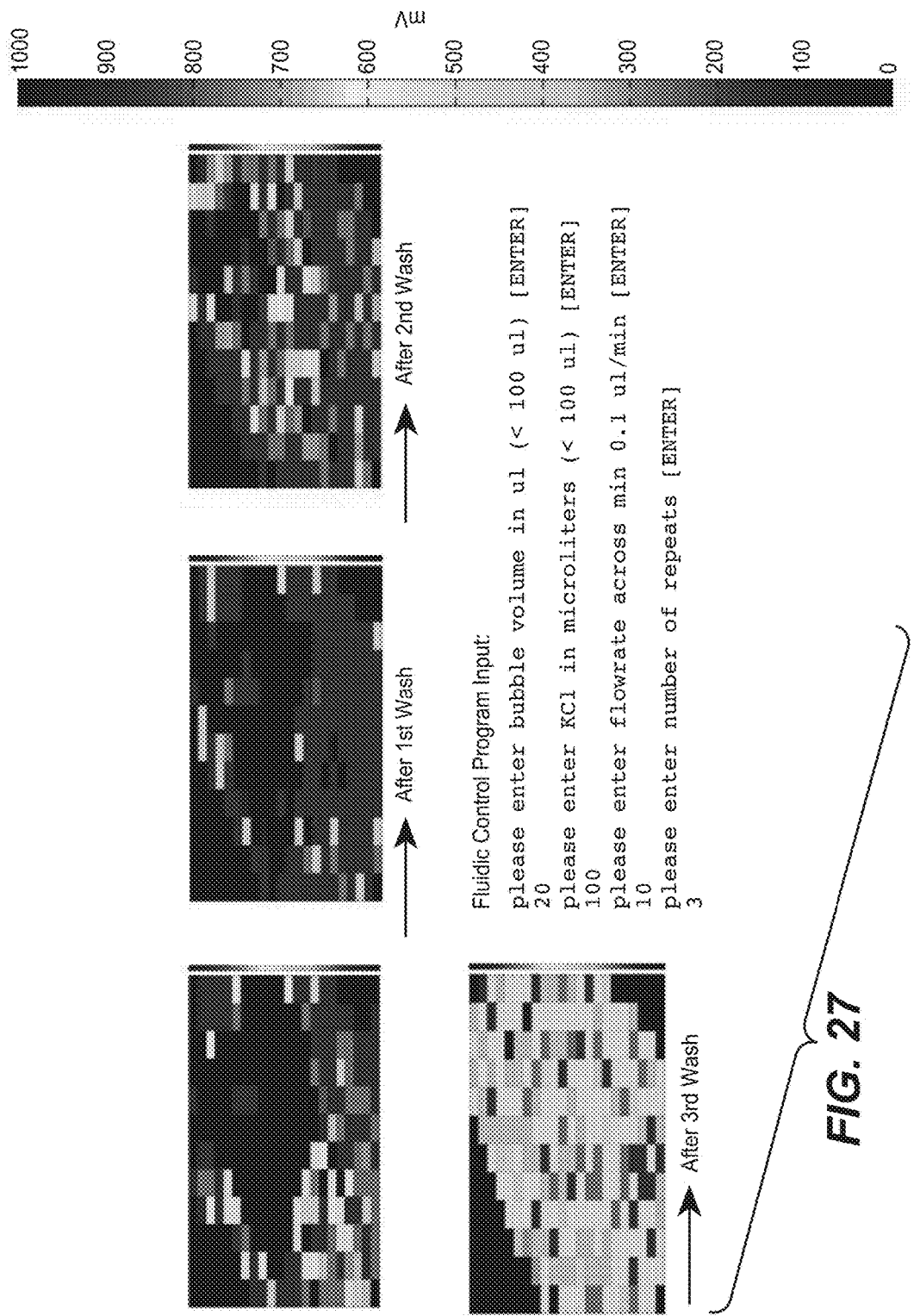
FIG. 27 shows an example of bilayer formation and pop automated with a pump.
Figure 28:
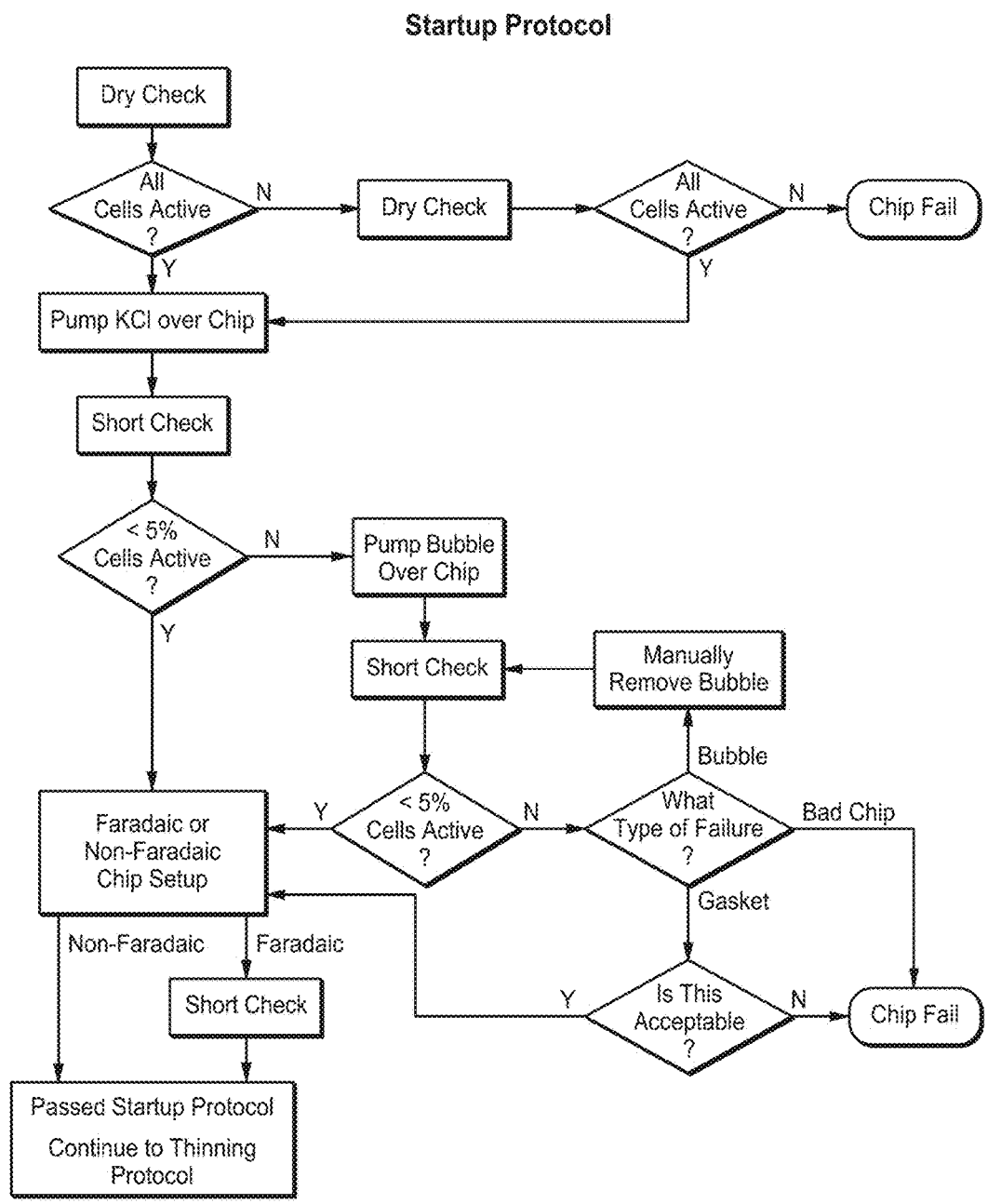
FIG. 28 is a flowchart for an automatic chip setup. This test would confirm that the majority of cells on the chip are acceptable. If an insufficient number of cells (as determined by the operator) pass the test, then the entire chip will fail.
Figure 29:
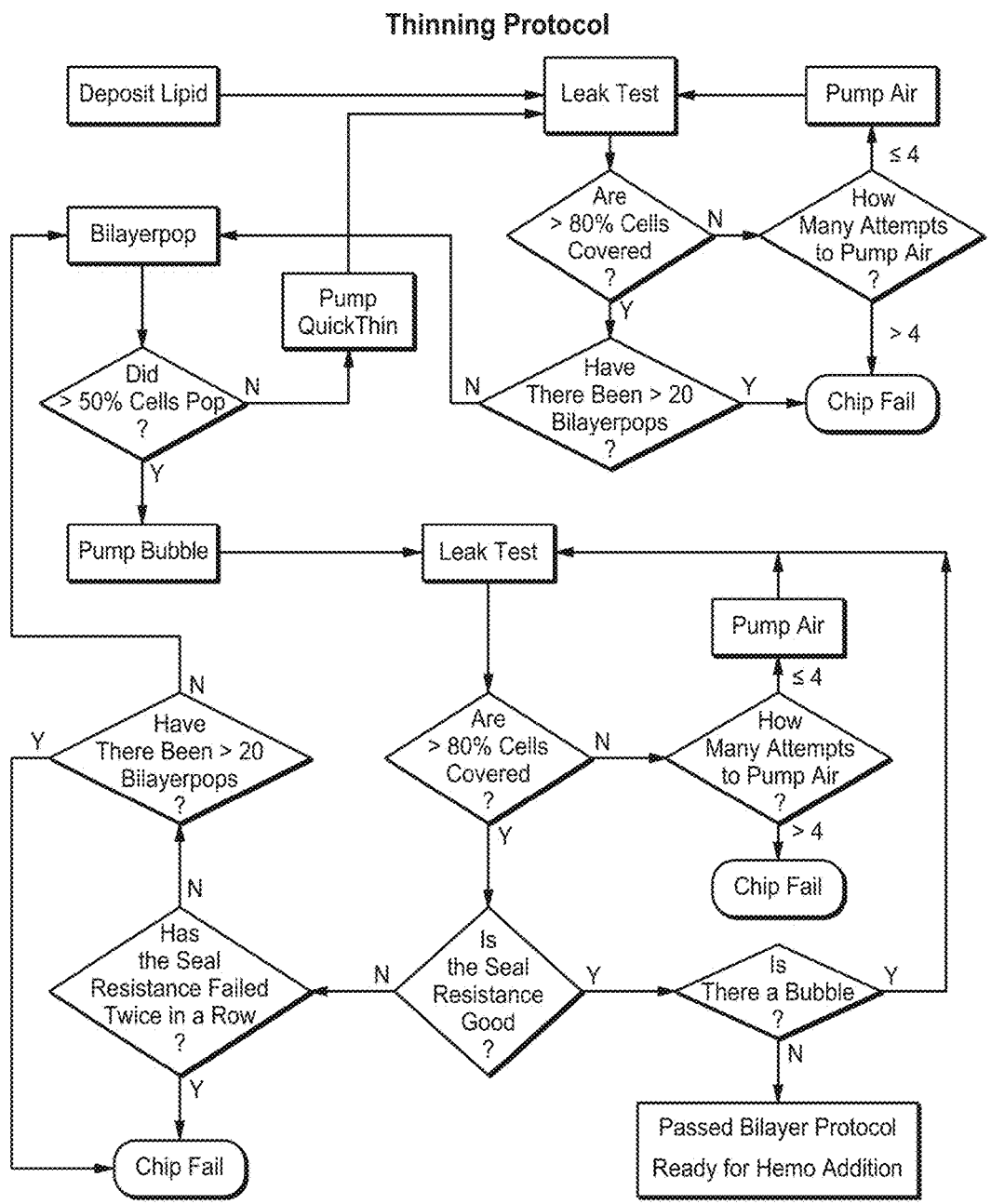
FIG. 29 is a flowchart for an automatic pump for bilayer formation.

FIG. 27 shows the voltage at which the bilayer pops vs. cell location under repeated bilayer generation and wash conditions. Automated bubble and KCl washing protocol allow consistent bilayer formation. Table 1 shows bilayer formation and pop yield under various conditions (e.g., with hemolysin and lipid or without hemolysin).

TABLE 1

| Bilayer formation and pop | | |
|---|---|---|
| Chip ID | % Covered | % Pop |
| 120830_CC 01-1 | 99% | 76% |
| 120824_CC 06-1 | 94% | 59% |
| 120801_CC 01-1 | 92% | 81% |
| 120803_MT 01-1 | 73% | 51% |

TABLE 1-continued

Bilayer formation and pop

| Chip ID | % Covered | % Pop |
|---|---|---|
| 120802_CC - 01-1 | 87% | 93% |
| 120731_MT 01-1 | 100% | 89% |
| 120803_MT 01-1 | 73% | 51% |

% Covered = number of cell that are covered by lipid at the beginning; not necessarily bilayer.
% Pop = number of electrodes that shorted the last time that the cells were popped.

Example 6: Fully Automated Bilayer Formation

This example provides a summary of the automated bilayer creation protocol for a chip. This protocol can be separated into two sections: startup, verifying and preparing the chip for the bilayer formation, and thinning, the actual bilayer formation on the chip.

Startup

The startup protocol has three main steps: a dry check, a short check and, optionally, conditioning. The dry check consists of applying voltages to each electrode to verify that none are giving anomalous data readings. This is typically done by applying a voltage pulse and counting cells that read current. If any actually give a current signal, then that electrode is deemed bad. If too many cells are bad, then the procedure ends. The next step is a short check. The desired salt/buffer solution is flowed on the chip and a voltage is applied to each electrode to verify that all are giving a short circuit reading. This is typically done by applying a voltage pulse and counting cells that give a railed reading. If not enough cells are good (i.e., give the railed reading), then the procedure ends. The last step in the startup protocol is the optional conditioning. This step is used for faradaic electrodes and exercises the electrodes to get them into a state that is ideal for electrochemistry. This is typically done by applying a series of voltage pulses and/or ramps to the cells.

Thinning

The thinning protocol has four main steps: the lipid addition, a leak test, a bilayer pop and a bilayer recovery. Coming out of the startup protocol, the chip is covered in the desired salt solution and the electrodes are in a good state for the rest of the experiment. The first step is to add lipid to the system. A small volume of the lipid/organic solvent mixture is flowed over the chip, followed by more salt solution. We then enter a loop of events, that exits when the thinning protocol has deemed the chip to have sufficient coverage and bilayer pops. The first part of the loop is a leak test. This test applies a staircase of increasing voltage, and tests cells for two things: whether or not it is covered by lipid material and if it is, what is the seal resistance of that coverage. If not enough cells are covered and have a high seal resistance, then a larger volume air bubble was flowed over the chip. This has been shown to increase our coverage across the chip. Another leak test followed this air bubble. This cycle will repeat until adequate coverage and seal resistance is measured or too many tests fail in a row, causing the procedure to end. Typically, it will pass after the first time and the procedure will move to the bilayer pop code. The bilayer pop code applies square waves of increasing voltage, all the way to ±1V. This is a destructive test that will pop bilayers, but covered cells without a bilayer will not pop. Typically, not enough pop on the first round was observed, so a bubble was flowed over the chip. Not to be bound by theory, it is believed that this bubble redistributes the lipid material, reforming bilayers over cells that popped, and also thinning out the lipid material over cells that did not. After rounds of leak tests, bilayer pops and bubbles, a threshold of popped cells will be hit, indicating that bilayers have been formed over the bulk of the cells. After the chip is deemed to be complete, the chip is ready for the insertion of nanopores.

Computer Implementation

The above protocol(s) may be automated and/or implemented on a computer system. The computer-implemented method for producing a lipid bilayer on biochip comprises:

a fluid dispensing device for selecting a fluid from a plurality of fluid reservoirs and for dispensing each fluid onto a biochip comprising a plurality of wells, wherein each fluid is dispensed in a preselected order;

a plurality of fluid reservoirs, each reservoir containing a fluid selected from a buffer, a lipid liquid, a wash liquid, a bubble generating system, wherein bubbles are provided at predetermined times;

an aspirator or gravity fed removal system for removing fluids from the plurality of wells of the biochip;

a biochip comprising a plurality of electrodes, said electrodes configured for detecting and/or determining a polymer sequence; and a control system for controlling the processing of the fluid and bubble cycling to form the lipid bilayer on the biochip.

The bubble generating system may be an opening to the air such that a bubble is created by pulling air from a valve port that is exposed to air, or by pulling gas from a valve port attached to a supply of a gas, and pushing it through the system.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for forming a lipid bilayer for use in a nanopore sensing device, comprising:
   (a) providing a primed chip comprising a fluid flow path in fluid communication with a plurality of sensing electrodes;
   (b) flowing a lipid solution into the fluid flow path; and
   (c) flowing at least one bubble onto the fluid flow path, thereby forming a lipid bilayer adjacent to the sensing electrodes, wherein the bubble spans the plurality of sensing electrodes.

2. The method of claim 1, wherein the bubble is adjacent to the sensing electrodes for at least about 5 milliseconds.

3. The method of claim 1, wherein the bubble is adjacent to the sensing electrodes for at least about 30 seconds.

4. The method of claim 1, wherein the bubble is adjacent to the sensing electrodes for at most about 5 minutes.

5. The method of claim 1, wherein a lipid bilayer is formed over at least 25% of the sensing electrodes.

6. The method of claim 1, further comprising inserting a nanopore into the lipid bilayers adjacent to each of the sensing electrodes.

7. The method of claim 1, wherein the chip comprises wells, and wherein the sensing electrodes are in the wells.

8. A method for forming a lipid bilayer for use in a nanopore sensing device, comprising:
   (a) providing a primed chip comprising a fluid flow path in fluid communication with a plurality of sensing electrodes;
   (b) flowing at least one bubble into the fluid flow path and adjacent to said plurality of sensing electrodes such that the bubble spans the plurality of sensing electrodes; and
   (c) contacting the periphery of the bubble with a lipid, wherein the lipid diffuses under the bubble and onto the fluid flow path, thereby forming a lipid bilayer adjacent to the sensing electrodes.

9. The method of claim 8, wherein the bubble is contacted with the lipid for at least about 5 milliseconds to about 10 minutes.

10. The method of claim 8, wherein a lipid bilayer is formed over at least 50% of the sensing electrodes.

11. The method of claim 8, further comprising inserting a nanopore into the lipid bilayers adjacent to each of the sensing electrodes.

12. The method of claim 6 or 11, wherein the nanopore is *Mycobacterium smegmatis* porin A (MspA), alpha-hemolysin, any protein having at least 70% homology to at least one of MspA or alpha-hemolysin, or any combination thereof.

13. The method of claim 6 or 11, wherein inserting the nanopore comprises applying a sequentially increasing electrical stimulus through said electrode to facilitate the insertion of said nanopore in said lipid bilayer.

14. The method of claim 1 or 8, wherein said lipid bilayer exhibits a resistance greater than about 1 GΩ.

15. The method of claim 6 or 11, wherein said lipid bilayer and said nanopore protein together exhibit a resistance of about 1 GΩ or less.

16. The method of claim 1 or 8, wherein said lipid comprises an organic solvent.

17. The method of claim 1 or 8, wherein said bubble is a vapor bubble.

18. The method of claim 1 or 8, wherein said lipid is selected from the group consisting of diphytanoyl-phosphatidylcholine (DPhPC), 1,2-diphytanoyl-sn-glycero-3 phosphocholine, 1,2-Di-O-Phytanyl-sn-Glycero-3-phosphocholine (DoPhPC), palmitoyl-oleoyl-phosphatidyl-choline (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy(polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-1000]; 1,2-dipalmitoyl-sn-glycero-3-phosphoethanolamine-N-[methoxy(polyethylene glycol)-2000]; 1,2-dioleoyl-sn-glycero-3-phosphoethanolamine-N-lactosyl; GM1 Ganglioside, Lysophosphatidylcholine (LPC) or any combination thereof.

19. The method of claim 8, wherein the chip comprises wells, and wherein the sensing electrodes are in the wells.

20. A nanopore sensing system, comprising:
   (a) a chip comprising a fluid flow path in fluid communication with a plurality of sensing electrodes, wherein each of said sensing electrodes is configured to detect an ionic current or change in resistance, conductance, charge, or voltage upon a nucleic acid incorporation or capture event; and
   (b) a control system coupled to said chip, said control system programmed to:
      i. flow an ionic solution across the chip followed by flowing a lipid solution into the fluid flow path;
      ii. flow at least one bubble into the fluid flow path and adjacent to the sensing electrodes for a time period of at least about 0.5 second, wherein the bubble spans the plurality of sensing electrodes, and wherein the flow of the bubble into the fluid flow path forms a lipid bilayer adjacent to the sensing electrodes.

21. The system of claim 20, wherein the chip comprises wells, and wherein the sensing electrodes are in the wells.

22. The system of claim 20, wherein the control system is external to said chip.

23. The system of claim 20, wherein the control system comprises a computer processor.

24. The system of claim 20, further comprising a fluid flow system operably coupled to said control system and said chip, wherein said fluid flow system is configured to direct the flow of said lipid solution and said bubble.

\* \* \* \* \*